(12) United States Patent
Schena et al.

(10) Patent No.: US 6,191,774 B1
(45) Date of Patent: Feb. 20, 2001

(54) MOUSE INTERFACE FOR PROVIDING FORCE FEEDBACK

(75) Inventors: Bruce M. Schena, Menlo Park; Louis B. Rosenberg, Pleasanton, both of CA (US)

(73) Assignee: Immersion Corporation, San Jose, CA (US)

( * ) Notice: Under 35 U.S.C. 154(b), the term of this patent shall be extended for 0 days.

(21) Appl. No.: 09/401,044

(22) Filed: Sep. 22, 1999

Related U.S. Application Data

(63) Continuation of application No. 08/881,691, filed on Jun. 24, 1997, which is a continuation-in-part of application No. 08/560,091, filed on Nov. 17, 1995, now Pat. No. 5,805,140, and a continuation-in-part of application No. 08/756,745, filed on Nov. 26, 1996, now Pat. No. 5,825,308.

(51) Int. Cl.[7] ....................................... G09G 5/08
(52) U.S. Cl. ........................... 345/163; 345/156; 345/184
(58) Field of Search .................. 345/156, 157, 345/160, 161, 163, 179, 184; 463/30, 37, 38; 434/45; 244/233

(56) References Cited

U.S. PATENT DOCUMENTS 5,555,894 * 9/1996 Doyama et al. ...................... 345/163
5,642,469 * 6/1997 Hannaford et al. .................. 345/179
5,754,433 * 5/1998 Fukui et al. .......................... 345/163
5,760,764 * 6/1998 Martinelli ............................. 345/160
5,990,869 * 11/1999 Kubica et al. ....................... 345/163

\* cited by examiner

*Primary Examiner*—Bipin Shalwala
*Assistant Examiner*—David L. Lewis
(74) *Attorney, Agent, or Firm*—James R. Riegel

(57) ABSTRACT

A force feedback mouse interface device connected to a host computer and providing realistic force feedback to a user. The mouse interface device includes a mouse object and a linkage coupled to the mouse that includes a plurality of members rotatably coupled to each other in a planar closed-loop linkage and including two members coupled to ground and rotatable about the same axis. Two actuators, preferably electromagnetic voice coils, provide forces in the two degrees of freedom of the planar workspace of the mouse object. Each of the actuators includes a moveable coil portion integrated with one of the members of the linkage and a magnet portion coupled to the ground surface through which the coil portion moves. The grounded magnet portions of the actuators can be coupled together such that a common flux path between the magnet portions is shared by both magnets. At least one sensor is coupled to the ground surface that detects movement of the linkage and provides a sensor signal including information from which a position of the mouse object in the planar workspace can be determined.

25 Claims, 23 Drawing Sheets

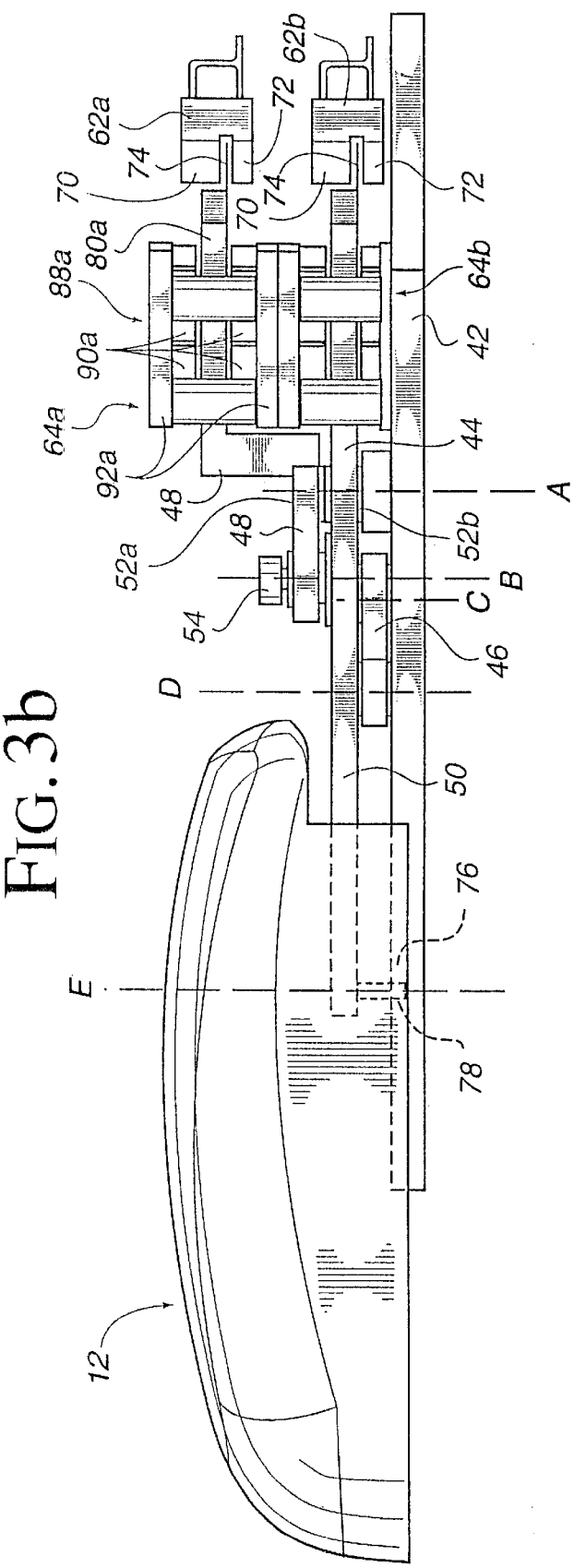

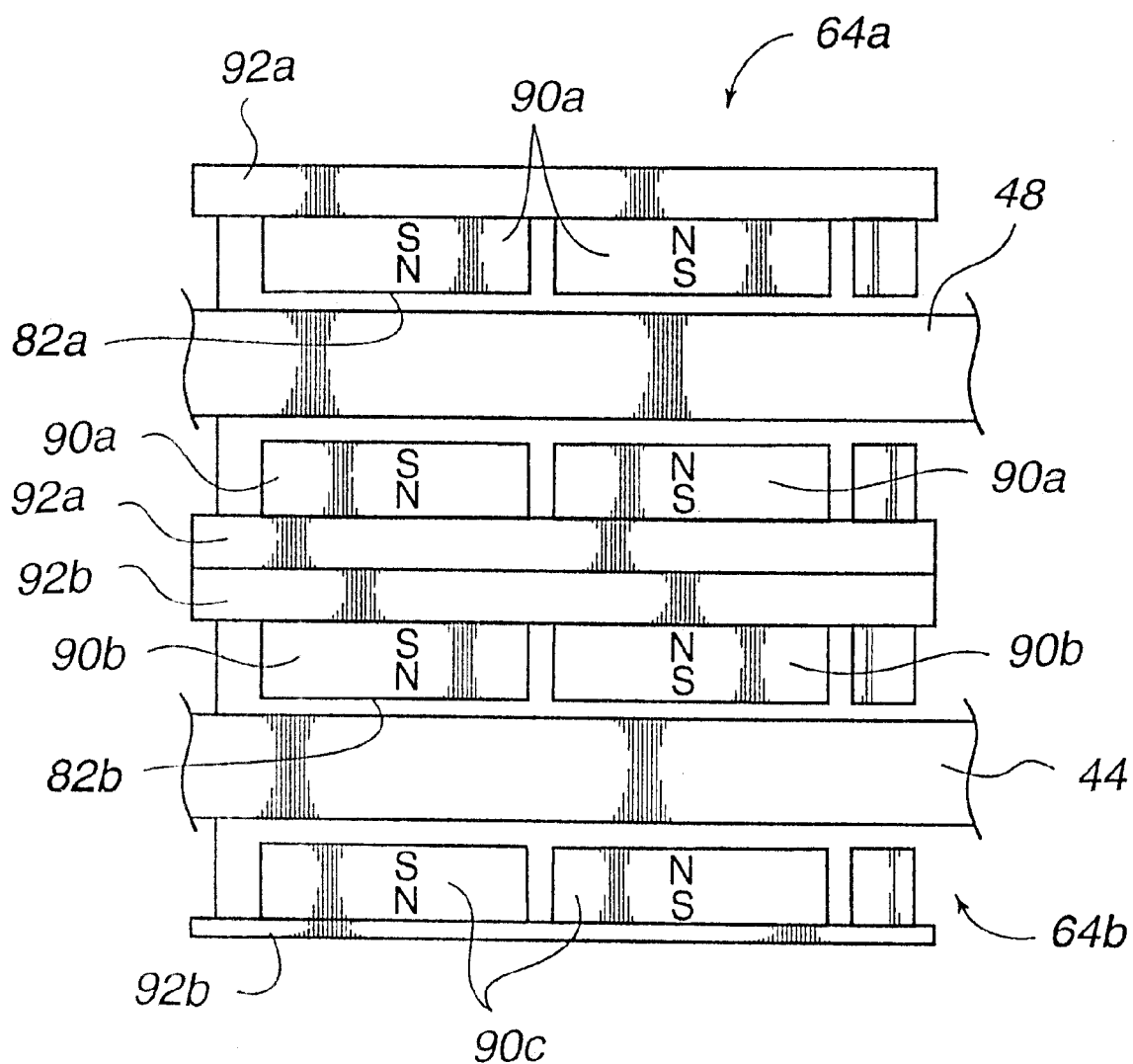

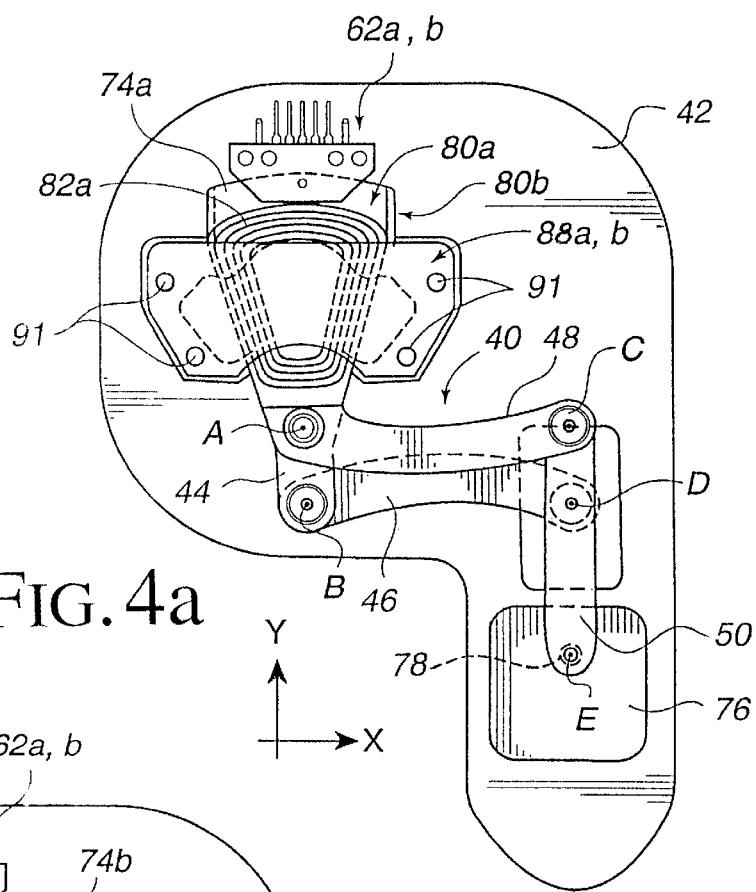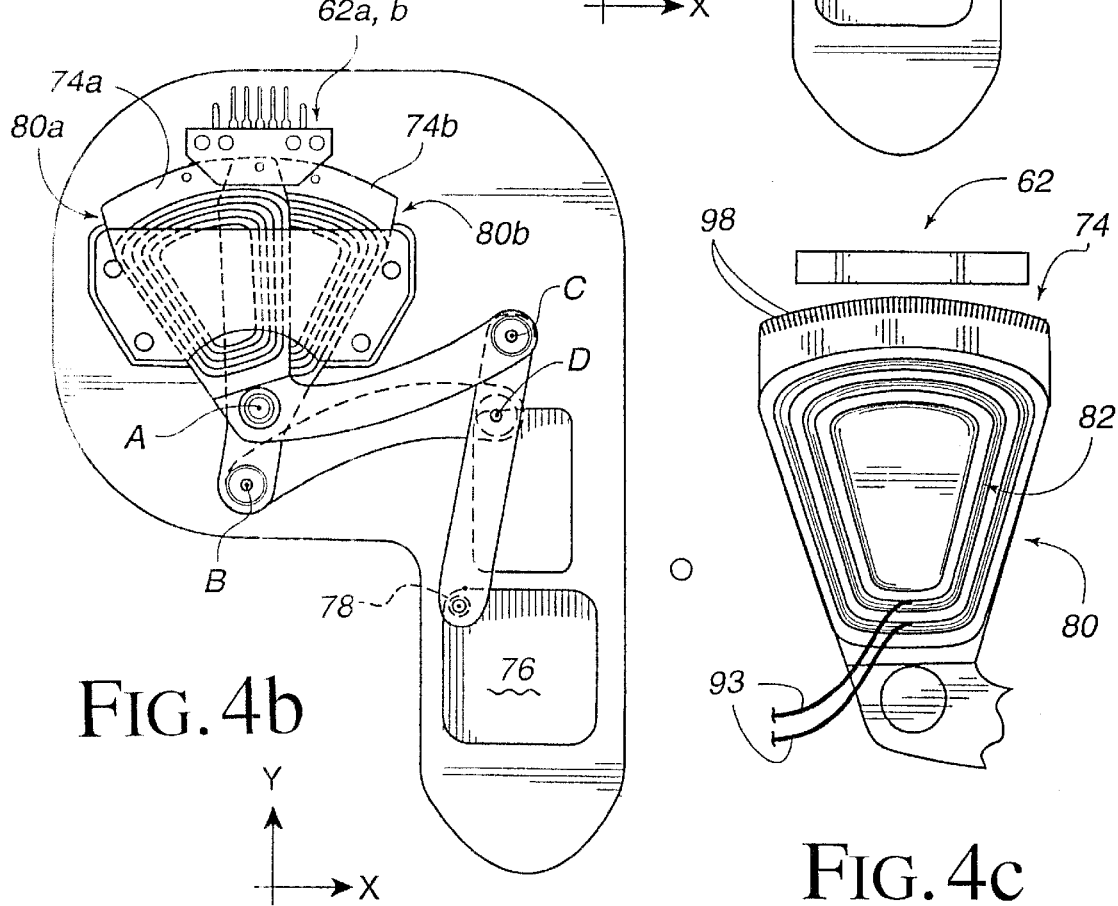
FIG. 4a
FIG. 4b
FIG. 4c

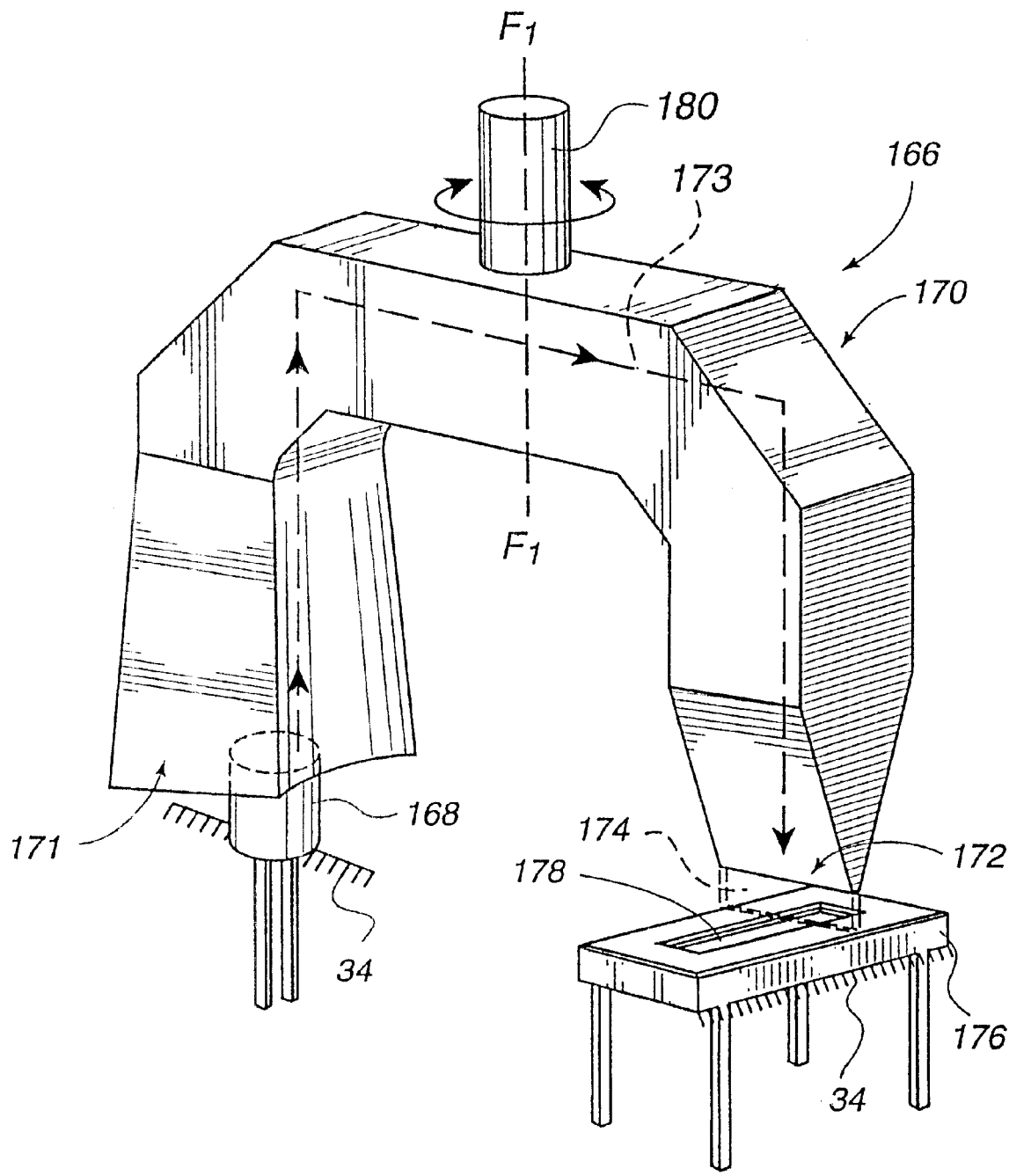
FIG. 4g1

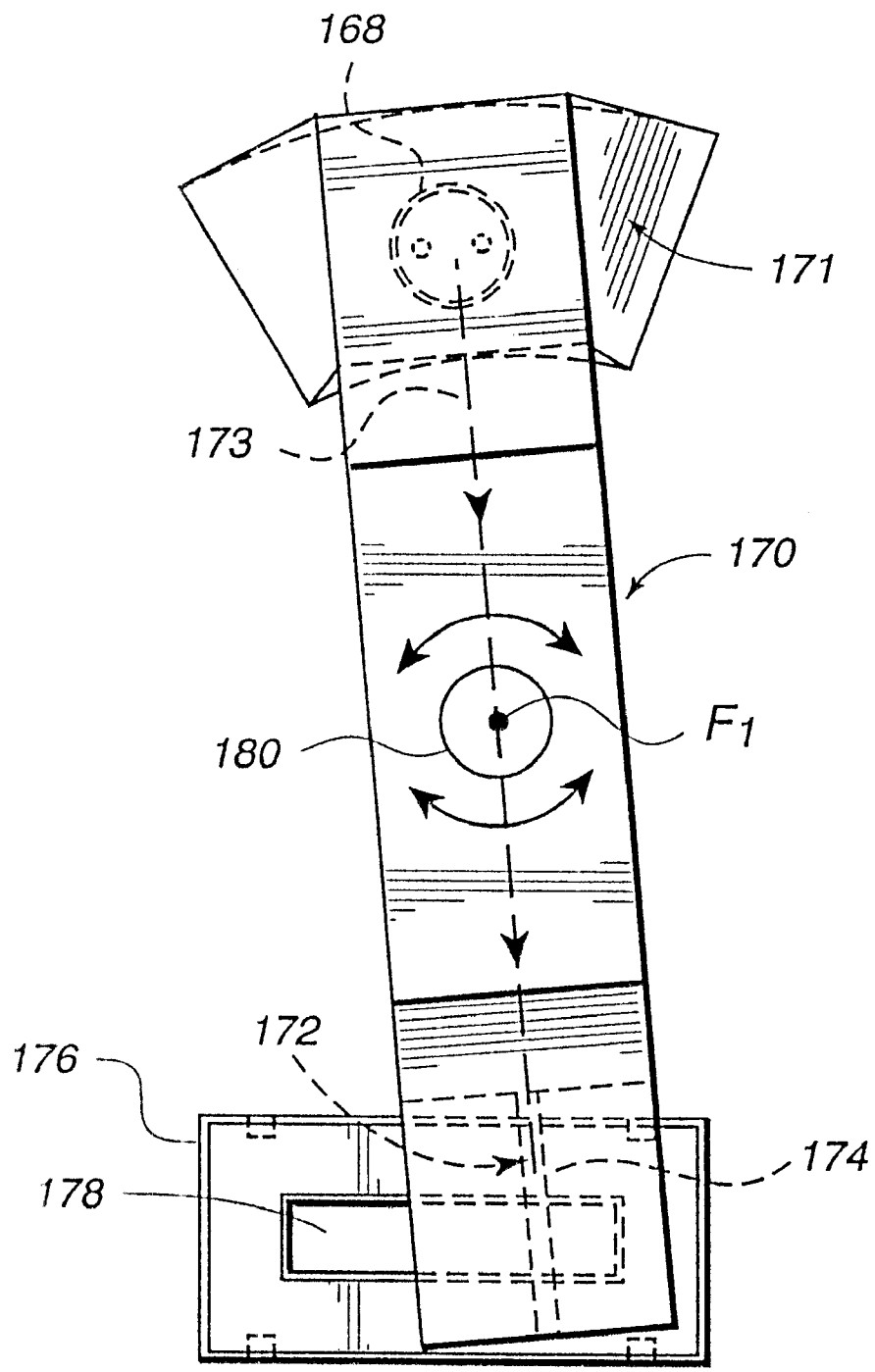
FIG. 4g2

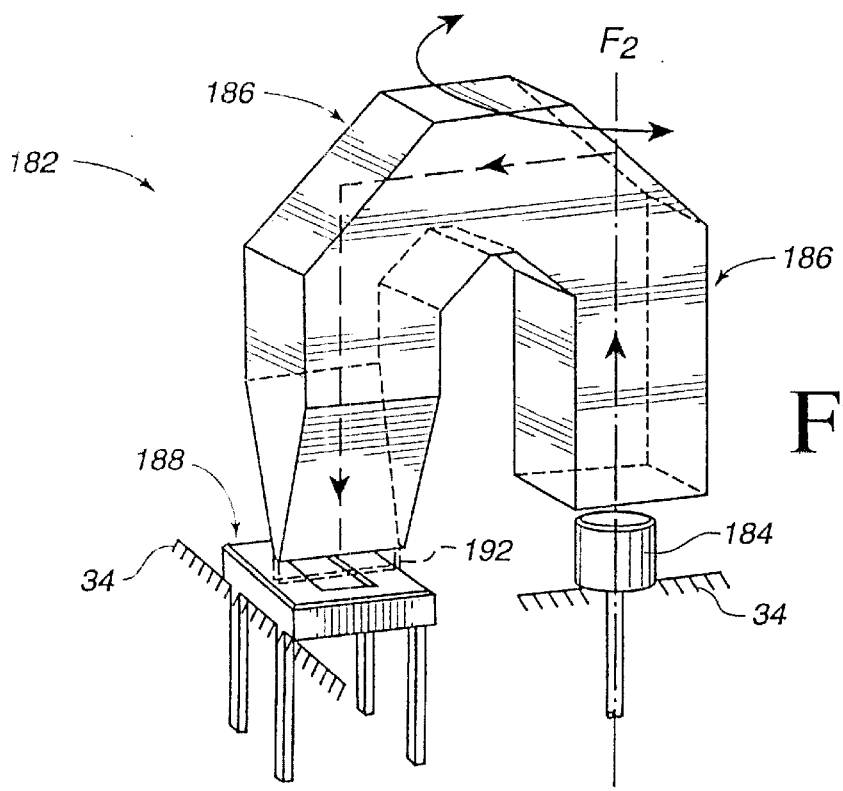
FIG. 4h1
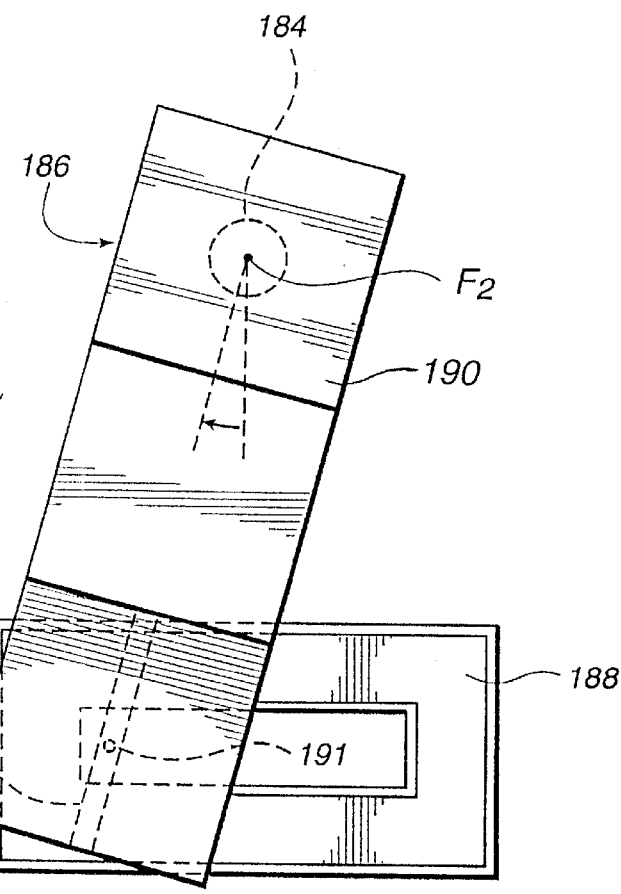
FIG. 4h2

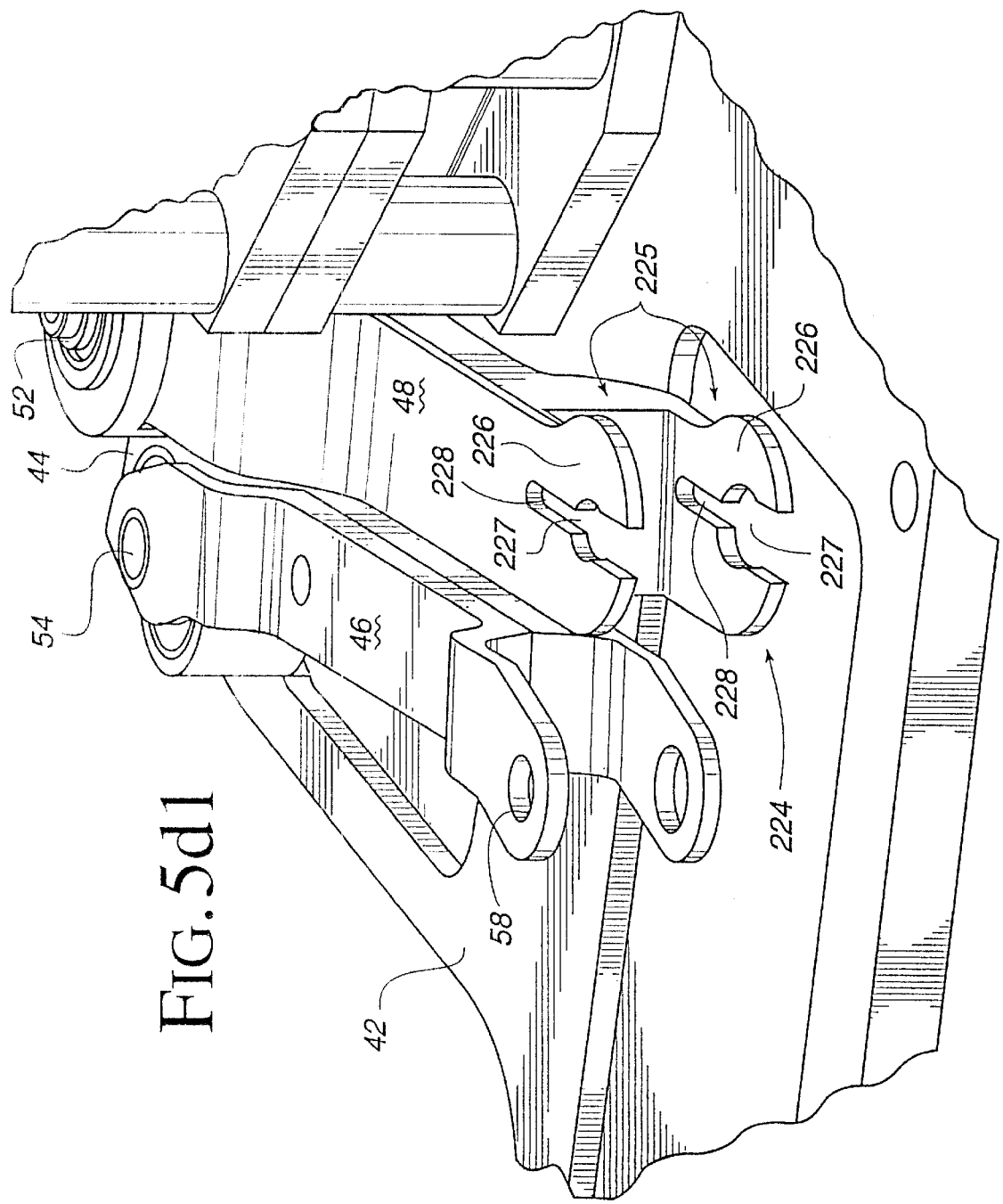

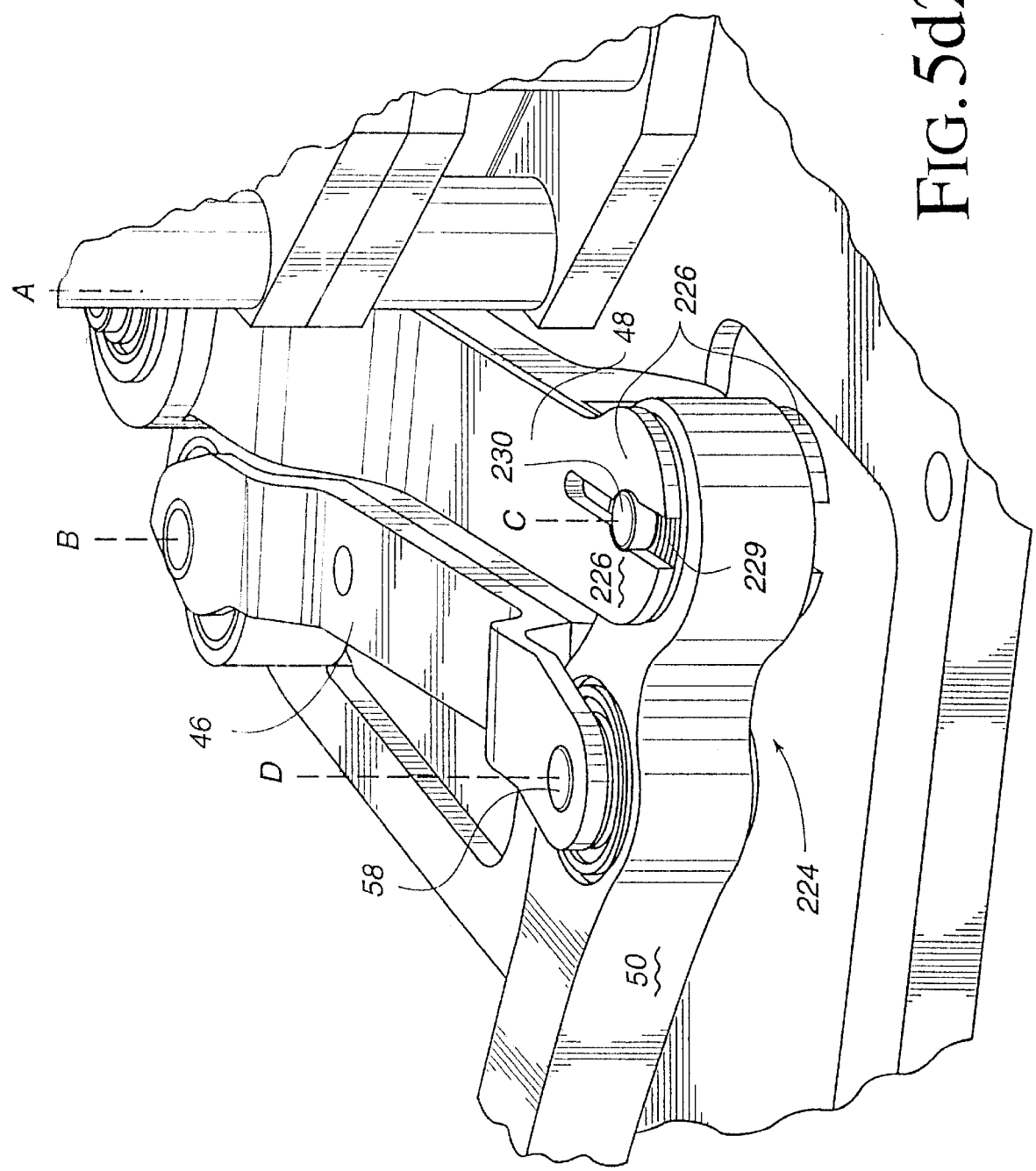
FIG. 5d2

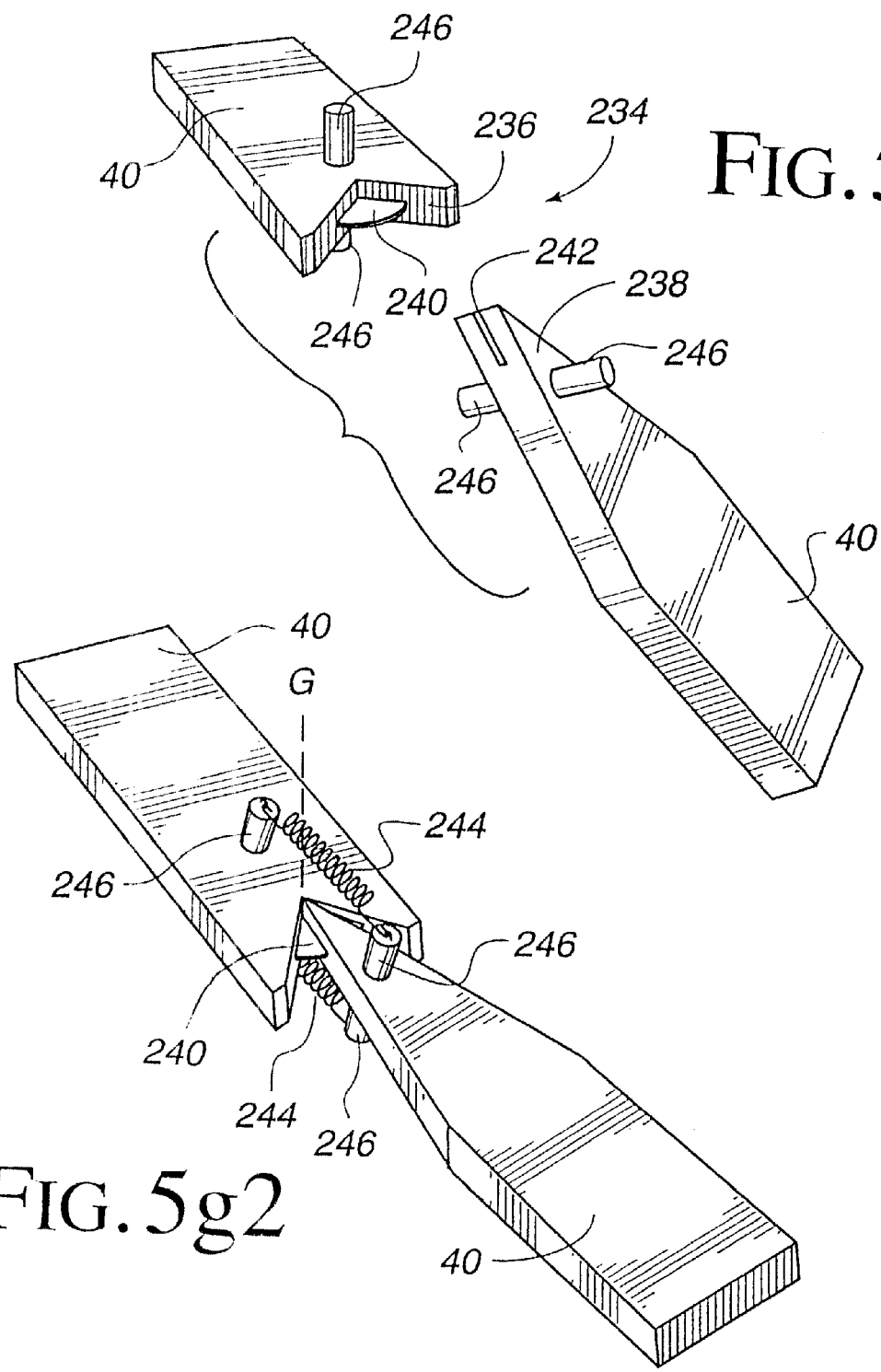

MOUSE INTERFACE FOR PROVIDING FORCE FEEDBACK

CROSS REFERENCE TO RELATED APPLICATIONS

This is a Continuation application of prior application Ser. No. 08/881,691 filed on Jun. 24, 1997, which is a continuation-in-part of parent patent application Ser. No. 08/560,091, now Pat. No. 5,805,140, filed Nov. 17, 1995, on behalf of Rosenberg et al., entitled "Method and Apparatus for Providing Low Cost Force Feedback and Mechanical I/O for Computer Systems", and Ser. No. 08/756,745, now Pat. No. 5,825,308, filed Nov. 26, 1996, on behalf of Rosenberg et al., entitled, "Force Feedback Interface having Isotonic and Isometric Functionality," both assigned to the assignee of this present application, and both of which are incorporated by reference herein.

This invention was made with Government support under Contract Number F41624-96-C-6029, awarded by the Department of Defense. The Government has certain rights in this invention.

BACKGROUND OF THE INVENTION

The present invention relates generally to interface devices for allowing humans to interface with computer systems, and more particularly to mechanical computer interface devices that allow the user to provide input to computer systems and provide force feedback to the user.

Computer systems are used extensively in many different industries to implement many applications, such as word processing, data management, simulations, games, and other tasks. A computer system typically displays a visual environment to a user on a display screen or other visual output device. Users can interact with the displayed environment to perform functions on the computer, play a game, experience a simulation or "virtual reality" environment, use a computer aided design (CAD) system, browse the World Wide Web, or otherwise influence events or images depicted on the screen.

One visual environment that is particularly common is a graphical user interface (GUI) GUI's present visual images which describe various graphical metaphors of a program or operating system implemented on the computer. Common GUI's include the Windows® operating system from Microsoft Corporation and the MacOS operating system from Apple Computer, Inc. These interfaces allows a user to graphically select and manipulate functions of the operating system and application programs by using an input interface device. The user typically moves a user-controlled graphical object, such as a cursor or pointer, across a computer screen and onto other displayed graphical objects or predefined screen regions, and then inputs a command to execute a given selection or operation. The objects or regions ("targets") can include, for example, icons, windows, pull-down menus, buttons, and scroll bars. Most GUI's are currently 2-dimensional as displayed on a computer screen; however, three dimensional (3-D) GUI's that present simulated 3-D environments on a 2-D screen can also be provided.

Other programs or environments that may provide user-controlled graphical objects such as a cursor include browsers and other programs displaying graphical "web pages" or other environments offered on the World Wide Web of the Internet, CAD programs, video games, virtual reality simulations, etc. In some graphical computer environments, the user may provide input to control a 3-D "view" of the graphical environment, i.e., the user-controlled graphical "object" can be considered the view displayed on the video screen. The user can manipulate the interface device to move the view, as if moving a camera through which the user is looking. This type of graphical manipulation is common in CAD or 3-D virtual reality applications.

The user interaction with and manipulation of the computer environment is achieved using any of a variety of types of human-computer interface devices that are connected to the computer system controlling the displayed environment. In most systems, the computer updates the environment in response to the user's manipulation of a user-manipulatable physical object ("user object") that is included in the interface device, such as a mouse, joystick, trackball, etc. The computer provides visual and audio feedback to the user utilizing the display screen and, typically, audio speakers.

Another mode of feedback recently introduced to the consumer home market is force feedback, which provide the user with sensory "haptic" (feel) information about an environment. Most of the consumer force feedback devices are joysticks which include motors to provide the forces to the joystick and to the user. Current force feedback joystick devices may allow realistic and effective forces to be transmitted to a user; however, the standard joystick device is well-suited for such uses as controlling an aircraft or other simulated vehicle in a simulation or game, first-person perspective virtual reality applications, or other rate-control tasks and is not well suited to position control tasks such as controlling a pointer or cursor in a graphical user interface. Other types of controllers, such a mouse, trackball, stylus and tablet, "touch point" keyboard pointers, and finger pads are commonly provided for cursor position control tasks since they are adept at accurately controlling the position of a graphical object in two dimensions. Herein, "position control" refers to a direct mapping of the position of the user object with a user-controlled graphical object, such as controlling a cursor in a GUI, while "rate control" refers to an indirect or abstract mapping of user object to graphical object, such as scrolling text in a window, zooming to a larger view in a window of a GUI, or controlling velocity of a simulated vehicle.

A problem with the currently-available position control interface devices is that none of them offer realistic force feedback. A mouse is not easily provided with force feedback since the mouse must be moved in a planar workspace and is not easily connected to actuators which provide the force feedback. Controllers as trackballs and tablets are even less well suited for force feedback than a mouse controller due to their free-floating movement. A joystick, in contrast, is typically connected to an immobile base which can include large actuators needed to provide realistic forces on the joystick. A mouse can be coupled to actuators from a side linkage, but a compact, low cost, and conveniently-positioned mechanism allowing free movement of a mouse as well as providing realistic force feedback for the mouse has not been available in the consumer market.

SUMMARY OF THE INVENTION

The present invention is directed to a mouse interface which is connected to a host computer and provides realistic force feedback to a user. The interface device includes low cost, compact components that provide a convenient mouse interface for a desktop.

More specifically, the present invention provides a mouse interface device for interfacing a user's motion with a host computer and providing force feedback to the user. The host computer preferably implements a graphical environment with which the user interacts using the mouse interface device. The mouse interface device includes a user object, preferably a mouse object, contacted and manipulated by a user and moveable in a planar workspace with respect to a ground surface. A linkage coupled to the mouse includes a plurality of members rotatably coupled to each other. In one preferred configuration, the linkage is a planar closed-loop linkage including two members coupled to ground and rotatable about the same axis. Two actuators, preferably electromagnetic voice coil actuators, provide forces in the two degrees of freedom of the planar workspace of the mouse object. Each of the actuators includes a moveable coil portion preferably integrated with one of the members of the linkage and a magnet portion coupled to the ground surface through which the coil portion moves. The actuators are controlled from commands output by the host computer. Finally, at least one sensor is coupled to the ground surface that detects movement of a member of the linkage and provides a sensor signal including information from which a position of the mouse object in the planar workspace can be determined.

The planar linkage may include four members coupled to a ground member, where a first base member is rotatably coupled to the ground member, a link member is rotatably coupled to the base member, a second base member is rotatably coupled to the ground member, and an object member is rotatably coupled to the link member and the second base member. The mouse object is coupled to the object member and preferably may rotate with respect to the object member to allow the user easy handling of the mouse. The members of the linkage are coupled together by bearings of the present invention, which may be ball bearing assemblies, snap together bearings, snap together bearings including ball bearings, or V-shaped bearings.

The coils of the actuators are preferably integrated in the members of the linkage, for example the base members of the linkage, and move through magnetic fields provided by the grounded portions. In addition, the grounded magnet portions of the actuators are coupled together in one embodiment, such that a common flux path between the magnet portions is shared by both magnet portions. In a preferred configuration, the first and second base members are coupled to a rotation point at a mid point of the base members, where one end of each base member integrates said coil such that the coil is spaced from the rotation point of said member, thereby providing mechanical advantage to forces generated by the actuator on the base members.

Many implementations of the sensor can be provided. In one embodiment, two sensors are provided, where the sensors are digital encoders that include a grounded portion having an emitter and detector and a moving portion on one of the members of the linkage including an encoder arc having a number of equally spaced marks provided, where the marks are detected by the grounded portion when the member moves. In other embodiments, the sensors can be lateral effect photo diodes, an emitter directing a beam to detector using a light pipe, an encoder sensor with a friction wheel, or a planar sensor pad. In one embodiment, the planar sensor pad senses a magnitude of force provided against the sensor pad in a direction perpendicular to the two degrees of freedom of the mouse object. Also, the wire coils and the grounded magnets of the actuators can be used as the sensor to sense a velocity of the members on which the coils are provided.

The mouse object is preferably rotatably coupled to the object member to allow convenient use of the mouse for the user such that the mouse object rotates about an axis of rotation though the object member, said axis of rotation being perpendicular to the ground surface. A stop mechanism limits movement of the mouse object in the planar workspace to a desired area, and can include a guide opening provided in the ground surface and a guide pin coupled to the linkage that engages sides of the guide opening to provide the movement limits. A safety switch can be included that causes the actuators to be deactivated when the user is not contacting the mouse object. A local microprocessor, separate from the host computer system, is included in the interface device and may provide local control over sensing and outputting forces to relieve the computational burden on the host computer. The interface device can also include a support such as a low friction Teflon pad, roller, or other member separate from the linkage and coupled between the mouse object and the ground surface for providing extra support to the mouse. An indexing feature of the present invention allows the user to change the offset between the position of the mouse object and the location of a displayed cursor on a display screen.

The method and apparatus of the present invention provides a force feedback mouse interface that allows a user to conveniently interface with a host computer application program. The actuators, sensors, and linkage of the device, in the embodiments described, provide a compact, simple, low-cost design that outputs realistic forces on the user and accurately tracks the user's motions in the provided workspace, and is well suited for the consumer market.

These and other advantages of the present invention will become apparent to those skilled in the art upon a reading of the following specification of the invention and a study of the several figures of the drawing.

BRIEF DESCRIPTION OF THE DRAWINGS

FIGS. 3a and 3b are top plan and side elevational views, respectively, of the mouse interface of FIG. 2;

FIG. 3c is a side elevational detail view of an actuator magnet assembly of the mouse interface of FIG. 2;

FIGS. 4a and 4b is a top plan view of the mouse interface of FIG. 2 in which the linkage is moved;

FIG. 4c is a detailed top plan view of the sensors used in the present invention;

FIGS. 4g1 and 4g2 are perspective and top plan views, respectively, of an alternate light pipe sensor of the present invention;

FIGS. 4h1 and 4h2 are perspective and top plan views, respectively, of an alternate light pipe sensor to that of FIGS. 4g1 and 4g2;

FIGS. 5d1 and 5d2 are perspective views of an alternate snap bearing of the present invention for use with the mouse interface of the present invention;

FIGS. 5g1 and 5g2 are perspective views of an alternate V-shaped bearing of the present invention for use with the mouse interface of the present invention;

FIG. 7c is a diagrammatic illustration of the indexing function of the present invention using the mouse of FIG. 7a.

DETAILED DESCRIPTION OF PREFERRED EMBODIMENTS

Figure 1:
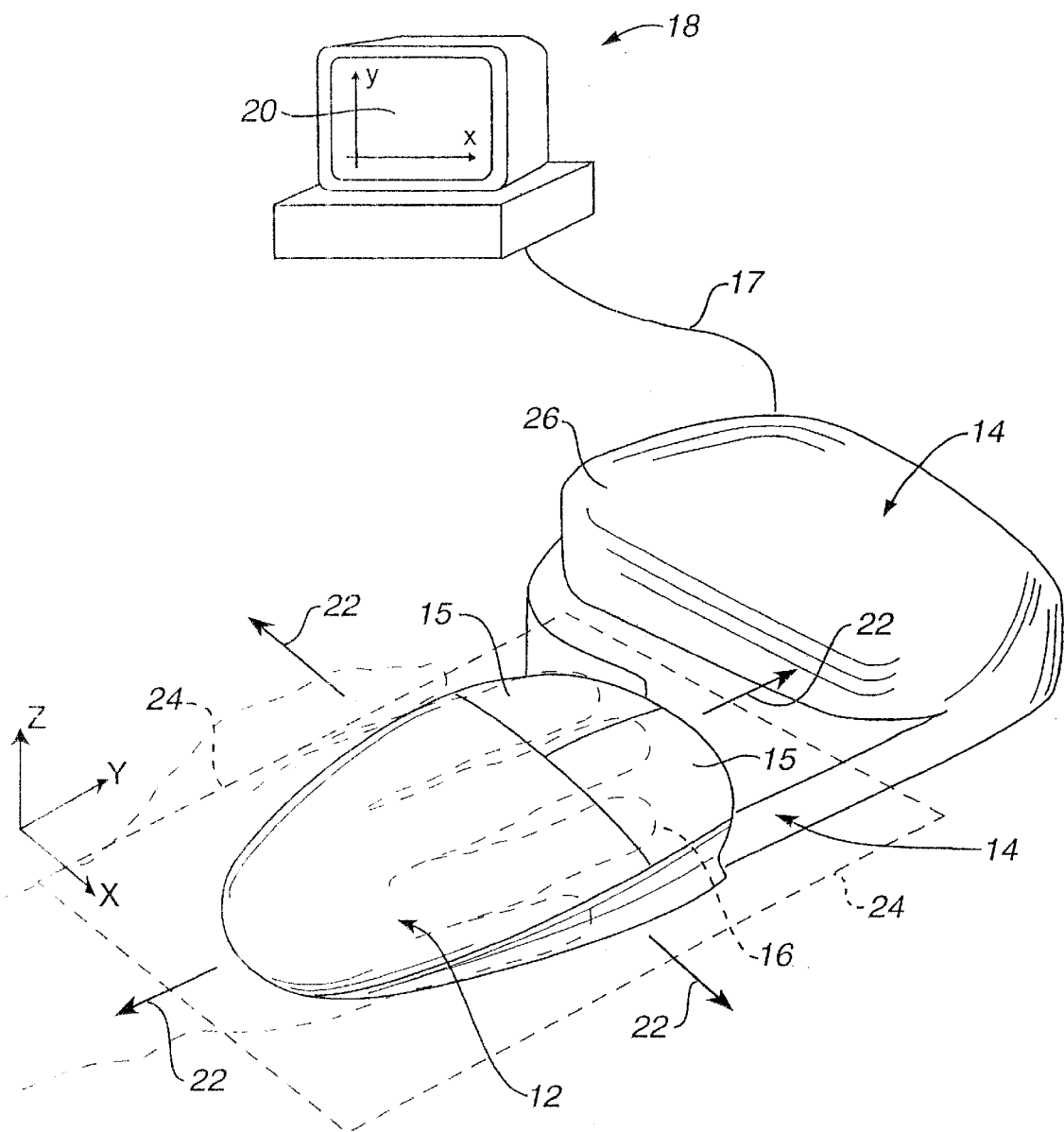
FIG. 1 is a perspective view of one embodiment of a force feedback mouse interface system of the present invention.

FIG. 1 is a perspective view of a force feedback mouse interface system 10 of the present invention capable of providing input to a host computer based on the user's manipulation of the mouse and capable of providing force feedback to the user of the mouse system based on events occurring in a program implemented by the host computer. Mouse system 10 includes a mouse or "puck" 12, an interface 14, and a host computer 18. It should be noted that the term "mouse" as used herein, indicates an object 12 generally shaped to be grasped or contacted from above and moved within a substantially planar workspace (and additional degrees of freedom if available). Typically, a mouse is a smooth or angular shaped compact unit that snugly fits under a user's hand, fingers, and/or palm.

Mouse 12 is an object that is preferably grasped or gripped and manipulated by a user. By "grasp," it is meant that users may releasably engage a portion of the object in some fashion, such as by hand, with their fingertips, etc. For example, images are displayed and/or modified on a display screen 20 of the computer system 18 in response to such manipulations. In the described embodiment, mouse 12 is shaped so that a user's fingers or hand may comfortably grasp the object and move it in the provided degrees of freedom in physical space; an example of a user's hand is shown as dashed line 16. For example, a user can move mouse 12 to correspondingly move a computer generated graphical object, such as a cursor or other image, in a graphical environment provided by computer 18. The available degrees of freedom in which mouse 12 can be moved are determined from the interface 14, described below. In addition, mouse 12 preferably includes one or more buttons 15 to allow the user to provide additional commands to the computer system.

It will be appreciated that a great number of other types of user manipulable objects ("user objects" or "physical objects") can be used with the method and apparatus of the present invention in place of or in addition to mouse 12. For example, such objects may include a sphere, a puck, a joystick, cubical- or other-shaped hand grips, a receptacle for receiving a finger or a stylus, a flat planar surface like a plastic card having a rubberized, contoured, and/or bumpy surface, or other objects. Some of these other objects, such as a stylus, are described in detail subsequently with respect to FIGS. 8a–e.

Interface 14 interfaces mechanical and electrical input and output between the mouse 12 and host computer 18 implementing the application program, such as a GUI, simulation or game environment. Interface 14 provides multiple degrees of freedom to mouse 12; in the preferred embodiment, two linear, planar degrees of freedom are provided to the mouse, as shown by arrows 22. In other embodiments, greater or fewer degrees of freedom can be provided, as well as rotary degrees of freedom. For many applications, mouse 12 need only be moved in a very small workspace area, shown as dashed line 24 in FIG. 1 as an example. This is described in greater detail with respect to FIG. 7c.

In a preferred embodiment, the user manipulates mouse 12 in a planar workspace, much like a traditional mouse, and the position of mouse 12 is translated into a form suitable for interpretation by position sensors of the interface 14. The sensors track the movement of the mouse 12 in planar space and provide suitable electronic signals to an electronic portion of interface 14. The interface 14 provides position information to host computer 18. In addition, host computer 18 and/or interface 14 provide force feedback signals to actuators coupled to interface 14, and the actuators generate forces on members of the mechanical portion of the interface 14 to provide forces on mouse 12 in provided or desired degrees of freedom. The user experiences the forces generated on the mouse 12 as realistic simulations of force sensations such as jolts, springs, textures, "barrier" forces, and the like.

For example, a rigid surface is generated on computer screen 20 and a computer object (e.g., cursor) controlled by the user collides with the surface. In a preferred embodiment, high-level host commands can be used to provide the various forces associated with the rigid surface. The local control mode using microprocessor 130 can be helpful in increasing the response time for forces applied to the user object, which is essential in creating realistic and accurate force feedback. For example, it is preferable that host computer 18 send a "spatial representation" to microprocessor 200, which is data describing the locations of some or all the graphical objects displayed in a GUI or other graphical environment which are associated with forces and the types/characteristics of these graphical objects. The microprocessor can store such a spatial representation in memory 204, and thus will be able to determine interactions between the user object and graphical objects (such as the rigid surface) independently of the host computer. In addition, the microprocessor 200 can be provided with the necessary instructions or data to check sensor readings, determine cursor and target positions, and determine output forces independently of host computer 18. The host could implement program functions (such as displaying images) when appropriate, and synchronization commands can be communicated between processor 200 and host 18 to correlate the microprocessor and host processes. Also, memory 204 can store predetermined force sensations for microprocessor 200 that are to be associated with particular types of graphical objects. Alternatively, the computer 18 can directly send force feedback signals to the interface 14 to generate forces on mouse 12.

The electronic portion of interface 14 may couple the mechanical portion of the interface to the host computer 18. The electronic portion is preferably included within the housing 26 of the interface 14 or, alternatively, the electronic portion may be included in host computer 18 or as a separate unit with its own housing. More particularly, interface 14 includes a local microprocessor distinct and separate from any microprocessors in the host computer 18 to control force feedback on mouse 12 independently of the host computer, as well as sensor and actuator interfaces that convert electrical signals to appropriate forms usable by the mechanical portion of interface 14 and host computer 18. A suitable embodiment of the electrical portion of interface 14 is described in detail with reference to FIG. 6.

The interface 14 can be coupled to the computer 18 by a bus 17, which communicates signals between interface 14 and computer 18 and also, in the preferred embodiment, provides power to the interface 14 (e.g. when bus 17 includes a USB interface). In other embodiments, signals can be sent between interface 14 and computer 18 by wireless transmission/reception. In preferred embodiments of the present invention, the interface 14 serves as an input/output (I/O) device for the computer 18. The interface 14 can also receive inputs from other input devices or controls that are associated mouse system 10 and can relay those inputs to computer 18. For example, commands sent by the user activating a button on mouse 12 can be relayed to computer 18 by interface 14 to implement a command or cause the computer 18 to output a command to the interface 14. Such input devices are described in greater detail with respect to FIGS. 5 and 6.

Host computer 18 is preferably a personal computer or workstation, such as an IBM-PC compatible computer or Macintosh personal computer, or a SUN or Silicon Graphics workstation. For example, the computer 18 can operate under the Windows™ or MS-DOS operating system in conformance with an IBM PC AT standard. Alternatively, host computer system 18 can be one of a variety of home video game systems commonly connected to a television set, such as systems available from Nintendo, Sega, or Sony. In other embodiments, home computer system 18 can be a "set top box" which can be used, for example, to provide interactive television functions to users, or a "network-" or "internet-computer" which allows users to interact with a local or global network using standard connections and protocols such as used for the Internet and World Wide Web. Host computer preferably includes a host microprocessor, random access memory (RAM), read only memory (ROM), input/output (I/O) circuitry, and other components of computers well-known to those skilled in the art.

Host computer 18 preferably implements a host application program with which a user is interacting via mouse 12 and other peripherals, if appropriate, and which can include force feedback functionality. For example, the host application program can be a simulation, video game, Web page or browser that implements HTML or VRML instructions, scientific analysis program, virtual reality training program or application, or other application program that utilizes input of mouse 12 and outputs force feedback commands to the mouse 12. Herein, for simplicity, operating systems such as Windows™, MS-DOS, MacOS, Unix, etc. are also referred to as "application programs." In one preferred embodiment, an application program utilizes a graphical user interface (GUI) to present options to a user and receive input from the user. Herein, computer 18 may be referred as displaying "graphical objects" or "computer objects." These objects are not physical objects, but are logical software unit collections of data and/or procedures that may be displayed as images by computer 18 on display screen 20, as is well known to those skilled in the art. A displayed cursor or a simulated cockpit of an aircraft might be considered a graphical object. The host application program checks for input signals received from the electronics and sensors of interface 14, and outputs force values and/or commands to be converted into forces on mouse 12. Suitable software drivers which interface such simulation software with computer input/output (I/O) devices are available from Immersion Human Interface Corporation of San Jose, Calif.

Display device 20 can be included in host computer 18 and can be a standard display screen (LCD, CRT, etc.), 3-D goggles, or any other visual output device. Typically, the host application provides images to be displayed on display device 20 and/or other feedback, such as auditory signals. For example, display screen 20 can display images from a GUI. Images describing a moving, first person point of view can be displayed, as in a virtual reality game. Or, images describing a third-person perspective of objects, backgrounds, etc. can be displayed. Alternatively, images from a simulation, such as a medical simulation, can be displayed, e.g., images of tissue and a representation of a manipulated user object 12 moving through the tissue, etc.

There are two primary "control paradigms" of operation for mouse system 10: position control and rate control. Position control is the more typical control paradigm for mouse and similar controllers, and refers to a mapping of mouse 12 in which displacement of the mouse in physical space directly dictates displacement of a graphical object. The mapping can have an arbitrary scale factor or even be non-linear, but the fundamental relation between mouse displacements and graphical object displacements should be present. Under a position control mapping, the computer object does not move unless the user object is in motion. Also, "ballistics" for mice-type devices can be used, in which small motions of the mouse have a different scaling factor for cursor movement than large motions of the mouse to allow more control of small cursor movement. Position control is not a popular mapping for traditional computer games, but is popular for other applications such as graphical user interfaces (GUI's) or medical procedure simulations. Position control force feedback roughly corresponds to forces which would be perceived directly by the user, i.e., they are "user-centric" forces.

As shown in FIG. 1, the host computer may have its own "host frame" 28 which is displayed on the display screen 20. In contrast, the mouse 12 has its own "local frame" 30 in which the mouse 12 is moved. In a position control paradigm, the position (or change in position) of a user-controlled graphical object, such as a cursor, in host frame 30 corresponds to a position (or change in position) of the mouse 12 in the local frame 28. The offset between the object in the host frame and the object in the local frame can preferably be changed by the user, as described below in FIG. 7c.

Rate control is also used as a control paradigm. This refers to a mapping in which the displacement of the mouse 12 along one or more provided degrees of freedom is abstractly mapped to motion of a computer-simulated object under control. There is not a direct physical mapping between physical object (mouse) motion and computer object motion. Thus, most rate control paradigms are fundamentally different from position control in that the user object can be held steady at a given position but the controlled computer object is in motion at a commanded or given velocity, while the position control paradigm only allows the controlled computer object to be in motion if the user object is in motion.

The mouse interface system 10 is useful for both position control ("isotonic") tasks and rate control ("isometric") tasks. For example, as a traditional mouse, the position of mouse 12 in the workspace 24 can be directly mapped to a position of a cursor on display screen 20 in a position control paradigm. Alternatively, the displacement of mouse 12 in a particular direction against an opposing output force can command rate control tasks in an isometric mode. An implementation that provides both isotonic and isometric functionality for a force feedback controller and which is very suitable for the interface device of the present invention is described in parent application Ser. No. 08/756,745, now Pat. No. 5,825,308, incorporated by reference herein.

Mouse 12 is preferably supported and suspended above grounded surface 34 by the mechanical portion of interface 14, described below. In alternate embodiments, mouse 12 can be moved on a grounded pad 32 or other surface. In other embodiments, mouse 12 can contact a surface, pad, or grounded surface 34 to provide additional support for the mouse and relieve stress on the mechanical portion of interface 14. In particular, such additional support is valuable for embodiments in which there is only one location of grounding (e.g., at one axis of rotation) for a mechanical linkage of the device, as in the embodiment of FIG. 2. In such an embodiment, a wheel, roller, Teflon pad or other device is preferably used on the mouse to minimize friction between the mouse and the contacted surface.

Mouse 12 can be used, for example, to control a computer-generated graphical object such as a cursor displayed in a graphical computer environment, such as a GUI. The user can move the mouse in 2D planar workspace to move the cursor to graphical objects in the GUI or perform other tasks. In other graphical environments, such as a virtual reality video game, a user can be controlling a computer player or vehicle in the virtual environment by manipulating the mouse 12. The computer system tracks the position of the mouse with sensors as the user moves it. The computer system may also provide force feedback commands to the mouse, for example, when the user moves the graphical object against a generated surface such as an edge of a window, a virtual wall, etc. It thus appears and feels to the user that the mouse and the graphical object are contacting real surfaces.

Figure 2:
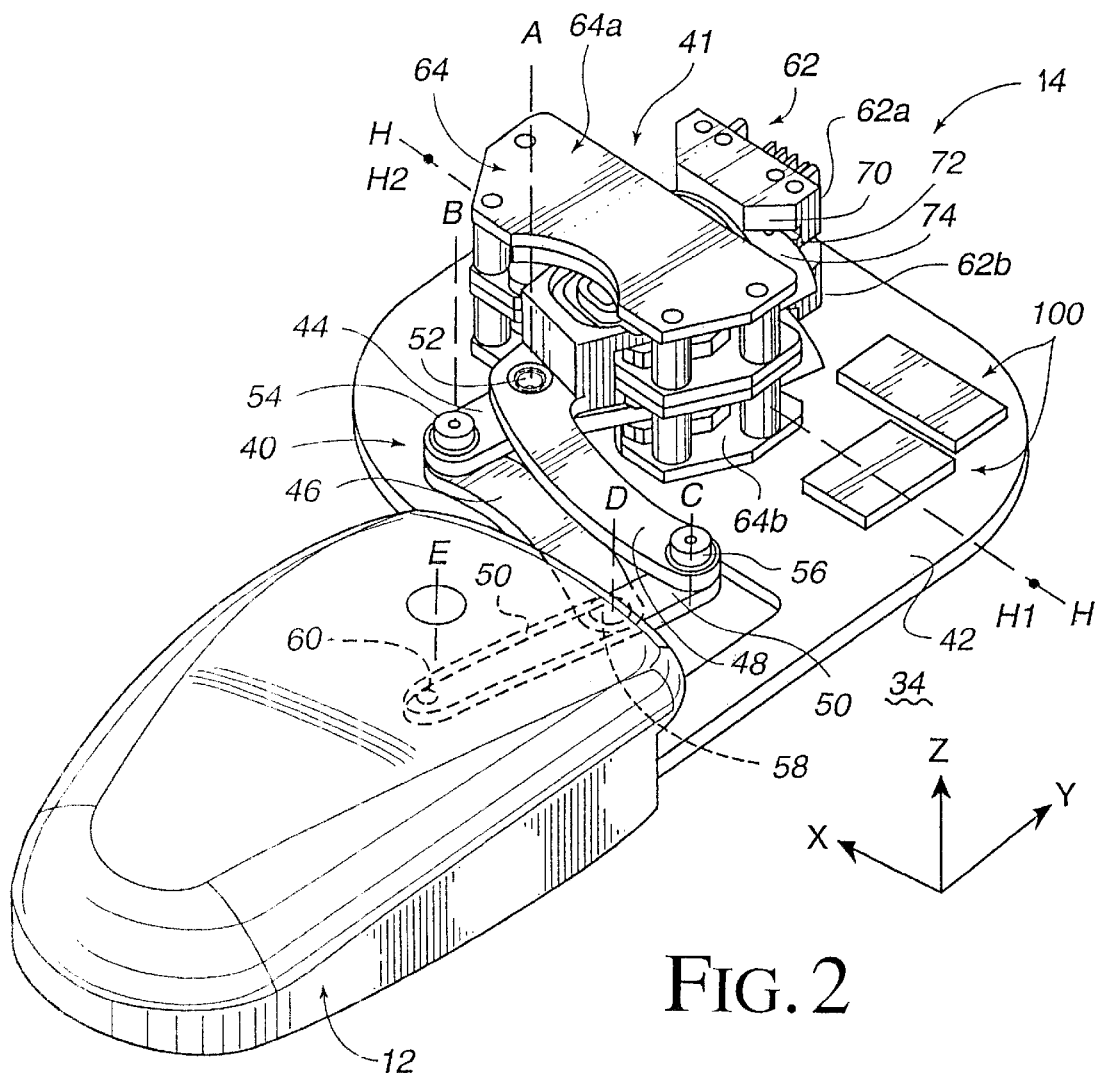
FIG. 2 is a perspective view of the mouse interface of FIG. 1 showing a linkage mechanism, actuators, and sensors of the present invention.

FIG. 2 is a perspective view of a preferred embodiment of the mouse system 10 with the cover portion of housing 26 removed, showing the mechanical portion of interface 14 for providing mechanical input and output in accordance with the present invention. Interface 14 includes a mouse or other user manipulatable object 12, a mechanical linkage 40, and a transducer system 41. A base 42 is provided to support the mechanical linkage 40 and transducer system 41 on grounded surface 34.

Mechanical linkage 40 provides support for mouse 12 and couples the mouse to a grounded surface 34, such as a tabletop or other support. Linkage 40 is, in the described embodiment, a 5-member (or "5-bar") linkage including a ground member 42, a first base member 44 coupled to ground member 42, a second base member 48 coupled to ground member 42, a link member 46 coupled to base member 44, and an object member 50 coupled to link member 46, base member 48 and to mouse 12. Fewer or greater numbers of members in the linkage can be provided in alternate embodiments.

Ground member 42 of the linkage 40 is a base for the support of the linkage and is coupled to or resting on a ground surface 34. The ground member 42 in FIG. 2 is shown as a plate or base that extends under mouse 12. In other embodiments, the ground member can be shaped in other ways and might only contact the ground surface directly under bearing 52, for example.

The members of linkage 40 are rotatably coupled to one another through the use of rotatable pivots or bearing assemblies having one or more bearings, all referred to as "bearings" herein. Base member 44 is rotatably coupled to ground member 42 by a grounded bearing 52 and can rotate about an axis A. Link member 46 is rotatably coupled to base member 44 by bearing 54 and can rotate about a floating axis B, and base member 48 is rotatably coupled to ground member 42 by bearing 52 and can rotate about axis A. Object member 50 is rotatably coupled to base member 48 by bearing 56 and can rotate about floating axis C, and object member 50 is also rotatably coupled to link member 46 by bearing 58 such that object member 50 and link member 46 may rotate relative to each other about floating axis D. In the described embodiment, link member 46 is coupled at its end to a mid-portion of object member 50 and mouse 12 is coupled to the end of object member 50. In an alternate embodiment, the end of link member 46 can be rotatably coupled to the end of base member 48, as in a parallel linkage disclosed in co-pending patent application Ser. No. 08/664,086 by Rosenberg et al., hereby incorporated by reference in its entirety. The axes B, C, and D (and E) are "floating" in the sense that they are not fixed in one position relative to ground surface 34 as is axis A. Preferably, the axes B, C, and D are all substantially parallel to each other.

One advantageous feature of the linkage 40 is that both base member 44 and base member 48 are rotatable about the same axis A. This is important to allow the compact actuator design of the present invention, as described in greater detail with reference to FIGS. 3a and 3b. Also this configuration dramatically simplifies the kinematic equations required to describe the motion of mouse 12 and provide forces to mouse 12 at the other end of the linkage. In alternate embodiments, members 44 and 48 can be coupled to ground member 42 at different locations and are rotatable about different axes, so that two grounded axes are provided about which each member rotates. In yet other embodiments, the ground member 42 can be positioned between the base members 44 and 48 on axis A.

Linkage 40 is formed as a five-member closed-loop chain. Each member in the chain is rotatably coupled to two other members of the chain. The five-member linkage is arranged such that the members can rotate about their respective axes to provide mouse 12 with two degrees of freedom, i.e., mouse 12 can be moved within a planar workspace defined by the x-y plane, which is defined by the x- and y-axes as shown in FIG. 2. Linkage 40 is thus a "planar" five-member linkage, since it allows the mouse 12 to be moved within a plane. In addition, in the described embodiment, the members of linkage 40 are themselves approximately oriented in a plane.

Mouse 12 in the preferred embodiment is coupled to object member 50 by a rotary bearing 60 so that the mouse may rotate about floating axis E and allow the user some flexible movement in the planar workspace. In alternate embodiments, motion about axis E may be sensed by sensors. In yet other embodiments, forces can be provided on mouse 12 about axis E using actuators. In the preferred embodiment, a pad or other support is provided under mouse 12 to help support the mouse 12, and is described in greater detail with respect to FIG. 2a.

In alternate embodiments, capstan drive mechanisms (not shown) can be provided to transmit forces and motion between electromechanical transducers and the mouse 12. One example of the user of capstan drives is shown in parent application Ser. No. 08/756,745. Capstan drive mechanisms provide mechanical advantage for forces generated by actuators without introducing substantial friction and backlash to the system. In alternate embodiments, mouse 12 can also be moved in an additional spatial degree of freedom using a rotatable carriage coupled between ground member 42 and base member 44. Such an embodiment is described in greater detail with reference to co-pending patent application Ser. No. 08/736,161, now Pat. No. 5,828,197, incorporated by reference herein in its entirety.

Transducer system 41 is used to sense the position of mouse 12 in its workspace and to generate forces on the mouse 12. Transducer system 41 preferably includes sensors 64 and actuators 66. The sensors 64 collectively sense the movement of the mouse 12 in the provided degrees of freedom and send appropriate signals to the electronic portion of interface 14. Sensor 62a senses movement of link member 48 about axis A, and sensor 62b senses movement of base member 44 about axis A. These sensed positions about axis A allow the determination of the position of mouse 12 using known constants such as the lengths of the members of linkage 40 and using well-known coordinate transformations. Member lengths particular to the interface device can be stored in local memory 134, such as EEPROM, to account for manufacturing variations among different interface devices; alternatively, variations of the particular link lengths from standard lengths can be stored in memory 204.

Sensors 62 are, in the described embodiment, grounded optical encoders that sense the intermittent blockage of an emitted beam. A grounded emitter portion 70 emits a beam which is detected across a gap by a grounded detector 72. A moving encoder disk or arc 74 is provided at the end of member 48 which blocks the beam in predetermined spatial increments and allows a processor to determine the position of the arc 74 and thus the member 48 by counting the spatial increments. Also, a velocity of member 48 based on the speed of passing encoder marks can also be determined. In one embodiment, dedicated electronics such as a "haptic accelerator" may determine velocity and/or acceleration, as disclosed in co-pending patent application Ser. No. 08/804,535, filed Feb. 21, 1997, and hereby incorporated by reference herein. The operation of sensors 62 are described in greater detail with reference to FIGS. 4a–4c.

Transducer system 41 also preferably includes actuators 64 to transmit forces to mouse 12 in space, i.e., in two (or more) degrees of freedom of the user object. The housing of a grounded portion of actuator 64b is rigidly coupled to ground member 42 and a moving portion of actuator 64b (preferably a coil) is integrated into the base member 44. The actuator transmits rotational forces to base member 44 about axis A. The housing of the grounded portion of actuator 64a is rigidly coupled to ground member 42 through the grounded housing of actuator 64b, and a moving portion (preferably a coil) of actuator 64a is integrated into base member 48. Actuator 64a transmits rotational forces to link member 48 about axis A. The combination of these rotational forces about axis A allows forces to be transmitted to mouse 12 in all directions in the planar workspace provided by linkage 40 through the rotational interaction of the members of linkage 40. The integration of the coils into the base members 44 and 48 is advantageous to the present invention and is discussed below.

In the preferred embodiment, actuators 64 are electromagnetic voice coil actuators which provide force through the interaction of a current in a magnetic field. The operation of the actuators 64 is described in greater detail below in FIG. 3. In other embodiments, other types of actuators can be used, both active and passive, such as DC motors, pneumatic motors, passive friction brakes, passive fluid-controlled brakes, etc.

Additional and/or different mechanisms can also be employed to provide desired degrees of freedom to mouse 12. For example, in some embodiments, bearing 60 can be provided between mouse 12 and mouse member 50 to allow the mouse to rotate about an axis E extending through the bearing 60. The allowed rotation can provided to allow the user's hand/wrist to conveniently stay in one position during mouse movement while the mouse 12 rotates about axis E. This rotational degree of freedom can also be sensed and/or actuated, if desired, to provide an additional control degree of freedom. In other embodiments, a floating gimbal mechanism can be included between mouse 12 and linkage 40 to provide additional degrees of freedom to mouse 12. Optionally, additional transducers can be also added to interface 14 in provided or additional degrees of freedom of mouse 12.

In an alternate embodiment, the mechanism 14 can be used for a 3-D interface device that allows a user to move a user object 12 in three dimensions rather than the 2-D planar workspace disclosed. For example, in one embodiment, the entire mechanism 14 can be made to rotate about a grounded axis, such as axis H extending through the magnet assemblies 88. For example, members (not shown) rigidly coupled to the magnet assemblies 88 or to grounded member 42 can extend in both directions along axis H and be rotary coupled to a grounded surface at points H1 and H2. This provides a third (rotary) degree of freedom about axis H to the mechanism 14 and to the user object 12. A motor can be grounded to the surface near point H1 or H2 and can drive the mechanism 14 about axis H, and a sensor, such as a rotary encoder, can sense motion in this third degree of freedom. One reason for providing axis H through the magnet assemblies is to reduce the inertia and weight contributed to motion about axis H by the magnet assemblies. Axis H can be provided in other positions in other embodiments. In such an embodiment, the user object 12 can be a stylus, grip, or other user object. A third linear degree of freedom to mechanism 14 can be provided in alternate embodiments. One embodiment of a planar linkage providing three degrees of freedom is disclosed in co-pending patent application Ser. No. 08/736,161 filed Oct. 25, 1996 and hereby incorporated by reference herein.

Figure 2A:
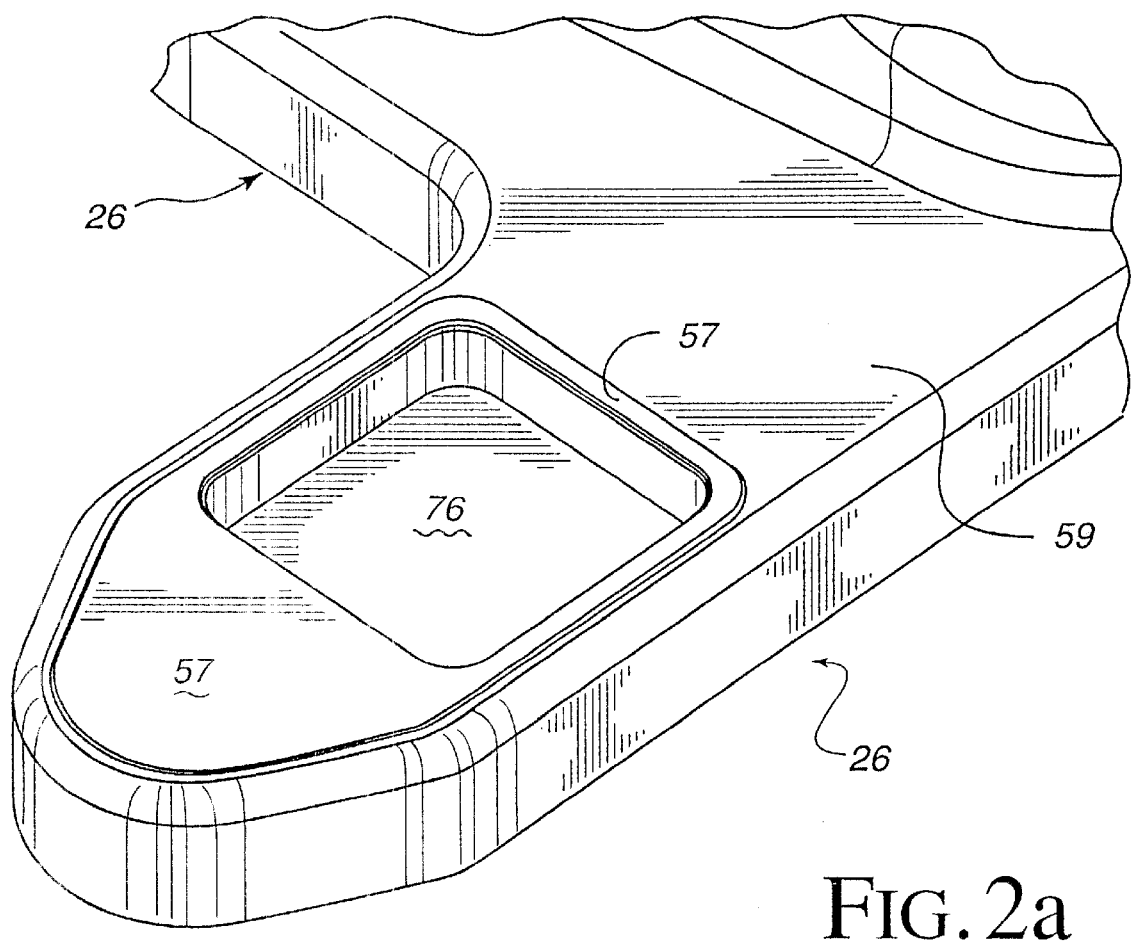
FIG. 2a is a perspective view of a support pad for supporting the mouse of FIG. 2.

FIG. 2a is a perspective view of a portion of the housing 26 of the mouse interface device of the present invention which is positioned under mouse 12. Grounded surface 59 of the housing 26 preferably includes, in the preferred embodiment, a pad 57 or other support positioned on it. Pad 57 supports the bottom of mouse 12 on the grounded surface 59 when the mouse is moved in its planar workspace. Since the linkage 40 is coupled to ground only at one location (axis A), the sideways position of the linkage 40 creates an unbalanced weight that may not be fully supported by the grounded bearing 52. Pad 57 provides the required support to any pressure or force from the user in the z-direction on mouse 12 toward the ground surface 34. In the described embodiment, the pad 57 surrounds an opening in housing 26 that is positioned over the opening 76 in the ground member 42 that provides the limits to the workspace of the mouse 12 using a guide pin, as described below (the ground member 42 is positioned under the surface 59 in the described embodiment).

The pad 57 can support the mouse 12 on any grounded surface, such as grounded member 42 or grounded surface 34. The pad 57 is preferably made of Teflon or other smooth material that allows the mouse 12 to slide substantially freely over surface 59 (or ground member 42 or grounded surface 34) with a small amount of friction. In other embodiments, other types of supports can be used that allow a small friction between mouse and surface, such as a roller, wheel, ball, etc. In other embodiments, a pad or other support can be coupled to the underside of linkage 40 such as at object member 50 or at bearing 60, or at other areas between mouse 12 and grounded surface 34.

Figure 3A:
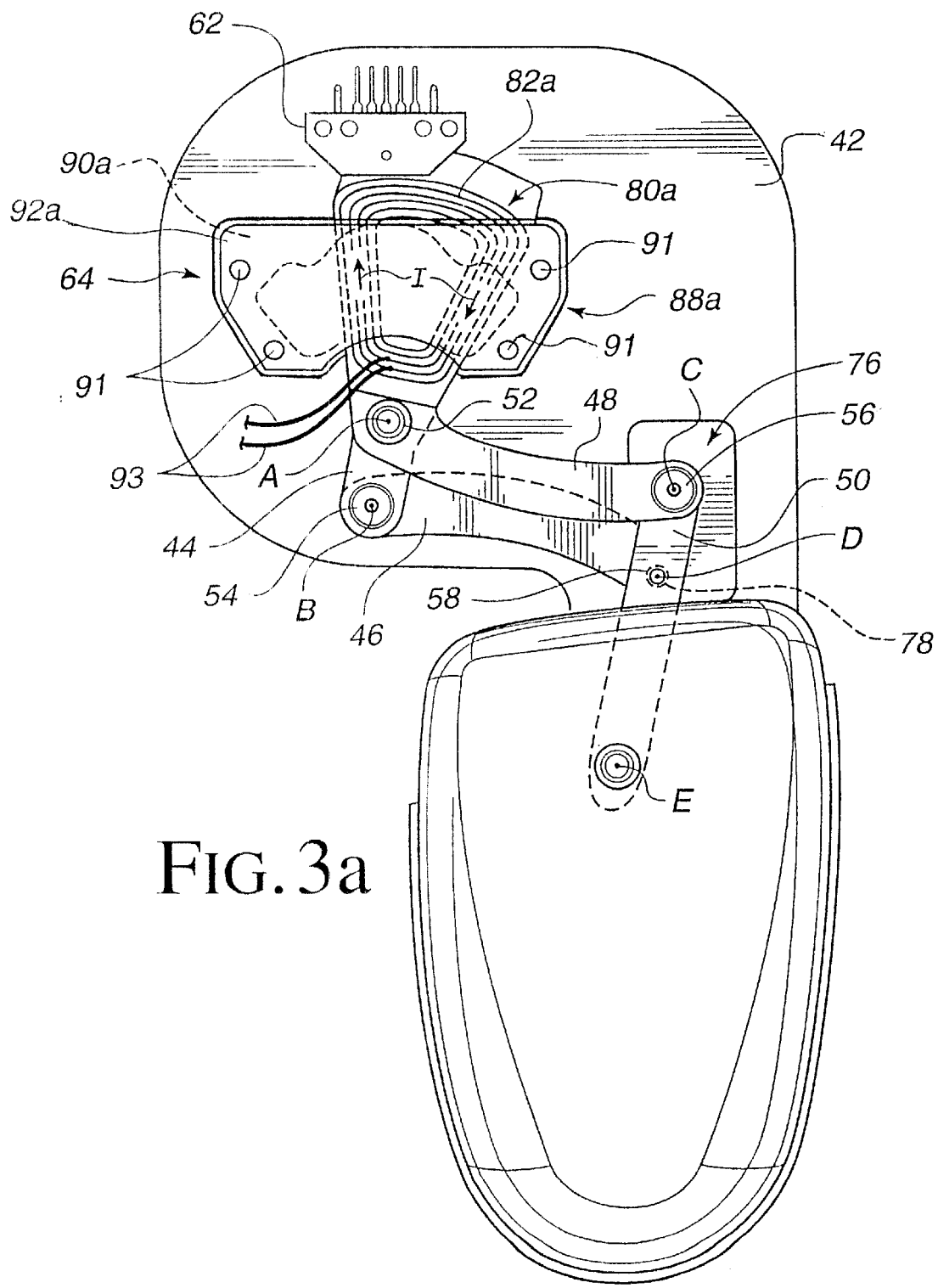

FIG. 3a is a top plan view and FIG. 3b is a side elevational view of the mouse interface system.

As seen in FIG. 3b, the only connection of the four linkage members 44, 46, 48, and 50 to the ground member 42 is through grounded bearing 52, where only base members 44 and 48 are grounded at axis A. Bearings 54, 56, and 58 are floating and not connected to the ground member. The single rotation point for the base members is important to the present invention since it allows the coils on the base members to sweep the same region, permitting the grounded portion of the actuators to be stacked as explained below. Bearing 52 actually includes two rotary bearings 52a and 52b, where bearing 52a couples member 48 to ground member 42 and bearing 52b couples member 44 to ground member 42.

As described above, actuators 64 are preferably electromagnetic voice coil actuators used to provide forces to the user object. The heavy portion of the actuators—the magnets and housing for magnets—are grounded, while the lighter portion of the actuators—the coils—are not grounded and ride on members of the linkage. Voice coil actuators are described in detail in parent patent application Ser. No. 08/560,091 now Pat. No. 5,805,140.

Actuator 64a drives base member 48. Base member 48 includes an integrated coil portion 80a on which a wire coil is provided. Coil portion 80a may be of the same material as the remaining portion of member 48, or it may include a circuit board material (with a suitable dielectric, etc.) which promotes easy layout and etching of a coil on its surface. A wire coil 82a of actuator 64a is coupled to portion 80a of member 48. Preferably, wire coil 82a includes at least two loops of wire and is etched or otherwise attached on portion 80a as a printed circuit board trace using well-known techniques. Fewer or greater numbers of loops of coil 82a can also be provided. Terminals 93 (shown better in FIG. 4c) from wire coil 82a to the electronic interface are provided so that computer 18 or local microprocessor 130 can control the direction and/or magnitude of the current in wire coil. The coil 82a can be made of aluminum, copper, or other conductive material.

The coil portion of actuator 64a is integrated in base member 48 and pivots about A as the base member so pivots. This feature is one of the advantages of the present invention. In typical prior art force feedback linkages, the actuator has a pivot/bearing which the actuator drives, which is separate from the bearing about which a member of the linkage rotates. In the device of the present invention, a single bearing 52 is a grounded bearing of the linkage and a guide bearing for the actuator, since base member 48 is part of both the linkage 40 and the actuator 64a. This is more efficient than having separate bearings since one part serves two functions, and reduces the weight of the device as well.

Voice coil actuator 64a also includes a magnet assembly 88a, which is grounded and preferably includes four magnets 90a and a plate flux path 92a. Alternatively, two magnets 90 with two polarities each can be included. As shown in FIG. 3c, each magnet has a polarity (north N or south S) on opposing sides of the magnet. Opposite polarities of magnets 90 face each other, such that coil 82a is positioned between opposing polarities on either side of the coil. In alternate embodiments, one or more magnets 90 can be provided on one side of coil 82a, and the other magnet 90 on the opposite side of the coil 82a can be a piece of metal shaped similarly to the magnet that provides a flux return path for the magnetic field. Preferably, a small amount of space is provided between the magnet surfaces and the coil 84a/member 48. Magnetic flux guide 92a is provided as, in the described embodiment, two steel plates on either side of the magnets 90a and are used to house the actuator 64a to allow magnetic flux from magnets 90a to travel from one end of the magnets 90a to the other end, as is well known to those skilled in the art.

The magnetic fields from magnets 90a interact with a magnetic field produced from wire coil 82a when current is flowed in coil 82a, thereby producing forces on member 48. Coil 82a and member 84 are positioned between magnets 90a and are thus affected by the magnetic fields of opposing magnets. As an electric current I is flowed through the coil 82a via electrical terminals 93, a magnetic field is generated from the current and configuration of coil 82a. The magnetic field from the coil then interacts with the magnetic fields generated by magnets 90a to produce a force on member 48 about axis A. The magnitude or strength of the force is dependent on the magnitude of the current that is applied to the coil, the number of loops in the coil, and the magnetic field strength of the magnets. The direction of the force depends on the direction of the current in the coil; the force can be applied in either direction about axis A. By applying a desired current magnitude and direction, force can be applied to member 48 and through member 50, thereby applying force to mouse 12 in the x-y plane workspace of the mouse. A voice coil actuator can be provided for each degree of freedom of the mechanical apparatus to which force is desired to be applied.

Thus, the magnetic fields from magnets 90a interact with the magnetic field produced from wire coil 82a when current is flowed in coil 82a to produce a planar force to the coil portion 80a of the member 84. The coil portion 80a and wire coil 82a are moved about axis A until the member 48 contacts the stop supports 91 provided at each end of the range of motion of the member 48 about axis A (guide opening 76 and guide pin 78 may also limit the range of the actuators; see FIG. 4a). Alternatively, the physical stops to movement can be omitted, where the force on member 48 is gradually decreases and ceases as the coil portion 80a moves out from between the magnets 90a.

Voice coil actuator 64b operates similarly to actuator 64a. A current is flowed through coil 82b to cause interaction with a magnetic field from magnets 90b of magnet assembly 88b which is similar to the magnet assembly 88a described above, and inducing magnetic forces that rotate portion 80b of base member 44 about axis A. This causes forces to be applied to mouse 12 in the x-y workspace of the mouse through the member 44, member 46, and member 50. In one embodiment, plates 90c provided on the other side of member 44 are simply metal plates provided for flux path of the magnetic field from magnets 90b (or are omitted altogether); this is more efficient from a manufacturing perspective since the magnets 90a and 90b are obtained as a unit and can simply be placed as is on the interface device 10 in the manufacturing process. In other embodiments, plates 90c can be magnets similar to magnets 90a and 90b; this provides a stronger magnetic field, allowing stronger forces using less power; however, the manufacturing/assembly process of the mouse interface device is more complex and expensive.

Magnet assembly 88b is preferably positioned below and coupled to magnetic assembly 88a such that the grounded magnet assemblies are stacked. Magnetic flux guide 92b is coupled to magnetic flux guide 92a and a portion of the flux path between the two magnetic assemblies is shared by both actuators. This allows each actuator to gain a greater flux path. In addition, the stacked configuration can provide both magnetic assemblies as a single unit, providing a more compact design, a simpler manufacturing design, less materials, and a simpler, less costly unit to mount on the interface device.

An important advantage of the present invention is the linkage 40 which provides a single rotation axis A for both base members 44 and 48. Since the base members 44 and 48 of the present invention also integrate the moving wire coil portion of the actuators, the moving portion of the actuators thus also rotate about the same axis A. The coils 82a and 82b thus sweep the same region, with one coil over the other coil. The members 44 and 48, in effect, act as guides for the movement of the coils. This single axis of rotation allows the magnet assemblies 88a and 88b to be stacked, which provides several advantages as explained above. The single axis rotation for both members 44 and 48 also allows the sensor arcs 74 to sweep out regions that are the same but on different points on the z-axis. This allows sensors 62a and 62b to be stacked on each other to read the sensor arcs, providing an even more advantageous, compact design.

A further advantage of integrating the coils 82 with the grounded base members 44 and 48 is that mechanical advantage is gained from the length of the base members. The two base members 44 and 48 are coupled to a single pivot point at a mid-point of the base members, where one end of each base member includes a coil—the coils are thus spaced from pivot. The mechanical advantage is derived from the ratio of the distance from the coil to the rotation point (axis A) and the distance from the rotation point to the other end of the member at the bearing 54. The base members 44 and 48 thus act as lever arms, and the lever arm distance provides mechanical advantage to forces generated by the actuators 64 and transmitted through linkage 40 to mouse 12.

The voice coil actuators 64a and 64b have several advantages. One is that a limited movement range is defined for a particular degree of freedom of mouse 12 by the length of the magnets 90 and the stops 91. Also, control of the voice coil actuator is simpler than other actuators since output torque is a substantially linear function of input coil current. In addition, since voice coil actuators do not require mechanical or electrical commutation as do other types of motors, the voice coil actuator has a longer life expectancy, less maintenance, and quiet operation. The actuation is nearly frictionless, resulting in greater haptic fidelity and smoother feel to the user. The parts for voice coil actuators are inexpensive to produce and are readily available, such as voice coil driver chips, resulting in a low cost way to provide realistic force feedback.

In the particular embodiment disclosed, another advantage relates to the grounding of both actuators 64a and 64b. Since both actuators are coupled to ground, the user moving mouse 12 does not carry the heavy portion of the actuators (the magnets and the housings) or feel their weight, thus promoting realistic force feedback using smaller magnitude forces, and allowing the interface system 10 to be a low cost device.

In alternate embodiments, the mechanical linkage 40 can be replaced by other mechanical linkages or structures which can provide desired degrees of freedom. For example, portions 80a and 80b of the members 48 and 44 can be linearly moved through encoders 62 and linear actuators can provide forces in linear degrees of freedom of mouse 12. In other embodiments in which rotary degrees of freedom are desired for a user object, linear degrees of freedom can be provided in the X and Y axes and can be converted to two rotary degrees of freedom for a user object 12 using a ball joint, pendulum, or other mechanism.

In the preferred embodiment, separate sensors 62 are used to detect the position of mouse 12 in its planar workspace. This is described in greater detail with respect to FIGS. 4a–4c. However, in alternate embodiments, the voice coil actuators 64a and 64b can also be used as sensors to sense the velocity of the members 44 and 48 about axis A and/or to derive the position and other values of mouse 12 in its planar workspace from the sensed velocity. Motion of coil 82a along axis Y within the magnetic field of magnets 90a induces a voltage across the coil 82a and this voltage can be sensed by an analog-to-digital converter or other electronics, for example. This voltage is proportional to the velocity of the coil and portion 80 of the rotating member about axis A. From this derived velocity, acceleration or position of the members 48 and 44 can be derived using timing information, for example, from a clock (described below). Alternatively, one or more additional coils similar to coil 82a and having an appropriate number of loops can be placed on member portions 80 which are dedicated to sensing voltage to derive position, velocity, or acceleration as described above. However, voice coil actuators produce analog values, which are subject to noise, and the filtering of such noise typically requires expensive components; thus, in the preferred low-cost embodiment, separate digital sensors are used to sense the position, motion, etc. of mouse 12.

In other embodiments, additional coils can also be provided for actuators 64 to provide different magnitudes of forces. For example, coil 82a can include multiple separate "sub-coils" of wire. A set of terminals can be included for each different sub-coil. Each sub-coil can include a different number of loops on portion 80 and therefore will generate a different magnetic field and thus a different magnitude of force when a constant current I is flowed through the sub-coil. This scheme is also applicable to a digital system using on and off switches. This embodiment is described in greater detail in co-pending application Ser. No. 08/560,091.

In other embodiments, linear actuators can be used to provide forces in provided degrees of freedom. Some examples of linear electromagnetic actuators are described in patent application Ser. No. 08/560,091. Also, other types of actuators may be used in place of or in addition to actuators 64 of the interface device. For example, the linkage can be driven by a direct drive DC motor or a geared/belt DC motor to provide mechanical advantage.

FIGS. 4a and 4b are top plan views of mouse interface system 10 showing the operation of the mouse system. In FIG. 4a, the mouse 12 (not shown) coupled to member 50 at axis E is approximately at a neutral position in which the members 44 and 50 are approximately parallel and the mouse is approximately in a center of its allowed workspace. Coil portions 80a and 80b of members 44 and 48 are approximately centered in the range of the optical encoder sensors 62a and 62b and within the range of magnet assemblies 88a and 88b.

As shown in FIG. 4a, a workspace guide opening 76 is provided in ground member 42 to limit the movement of mouse 12 in the x-y plane. Guide opening 76 is a shallow opening in the ground member 42 having sides which block movement of the mouse 12 beyond specified limits. A guide pin 78 is coupled to the bearing 60 at axis E and extends down into the guide opening 76. Pin 78 contacts one or more sides of the opening 76 when the mouse is moved to a limit in a particular direction. As shown, guide opening 76 has relatively small dimensions, allowing the mouse a workspace of approximately 0.9" by 0.9" in the described embodiment. This is typically adequate workspace for the user to move the mouse and control a graphical object such as a cursor on a display screen. In other embodiments, differently-sized guide openings can be provided for differently-sized workspaces, or other types of stops or guides can be used to prevent movement past predetermined limits. The guide opening 76 is shown as square shaped, but it can be rectangular in other embodiments; for example, the dimensions of opening 76 can be made the same aspect ratio as a standard computer monitor or other display screen. FIG. 4a shows guide pin 78 approximately in the center of the guide opening 76.

In FIG. 4b, the mouse 12 (not shown) and axis E have been moved in the x-y plane of the workspace of the mouse. The movement of the mouse has been limited by the guide opening 76, where guide pin 78 has engaged the sidewall of the upper-left corner area of guide opening 76 and stops any further movement in the forward y-direction. Linkage 40 and portions 80 of members 44 and 48 have moved as shown, such that portion 80a of link member 48 has moved to the left and portion 80b of base member 44 has moved to the right of their positions in FIG. 4a. Sensor 62a has detected the movement of portion 80a by sensing the movement of the encoder arc 74a through the gap of the encoder 62a. Likewise, sensor 62b has detected the movement of portion 80b by sensing the movement of the encoder arc 74b through the gap of encoder 62b.

FIG. 4c is a detailed top plan view of portion 80a of link member 48 and encoder 62a. Encoder arc 74 is preferably a transparent material, such as plastic, and preferably includes a number of dark line marks 98 which are very closely spaced together. The more closely spaced the marks 98 are, the finer the resolution of the sensor 62. For example, in the preferred embodiment, a line spacing on the arc can be about 200–500 lines per inch, providing four times that resolution in a quadrature encoder (these dimensions are exaggerated in FIG. 4c for clarity). Sensor 62 emits a beam of electromagnetic energy, such as an infrared beam, from emitter 70, which is detected across the gap at detector 72 when a mark 98 is not positioned to block the beam, i.e., the beam can travel through the transparent material of arc 74. When a mark passes under the beam, the beam is blocked and this blockage is detected by the detector 72. In this way, the detector 72 outputs a sensor signal or pulse indicating each time a mark passes through the beam. Since sensor 62 in the described embodiment is a quadrature encoder, detector 72 preferably includes 2 individual spaced apart detectors providing four times the resolution, as is well known to those skilled in the art. By counting the number of marks passing through the beam, the position of the member 48 about axis A is known. The velocity and/or acceleration of the member 48 can also be derived from the position data and timing information, as described above. Other types of emitter-detector pairs can also be used.

Portion 80b of base member 44 and encoder 62b function similarly to the portion 80a and encoder 62a described above. From the positions of the base member 48 and the base member 44 about axis A, the position of mouse 12 can be determined. A suitable optical quadrature encoder which performs the functions described above is model HEDS-9000 from Hewlett Packard. In alternate embodiments, the encoder wheel 158 may be made opaque, while marks 159 are notches cut out of the wheel 158 that allow the beam from the emitter to pass through and be detected by detector 162.

Alternate embodiments can include sensors 62a and/or 62b (and/or actuators 64) in different positions. For example, as shown in the alternate embodiment of FIG. 4d, the actuators 64a and 64b can be placed on opposing sides of the grounded axis A. Likewise, sensors 62a and 62b are placed with their corresponding actuators. Linkage 40' includes the members 44, 46, 48, and 50 as in the embodiment of FIG. 2, but in slightly different positions due to the different sensor/actuator placement. In other respects, the embodiment of FIG. 4d operates similarly to the embodiment of FIG. 2. In other embodiments, actuators 64 and sensors 62 can also be placed in other positions.

In other embodiments, other types of sensors can be used. For example, a single sensor can be used to detect motion in both degrees of freedom.

Figure 4D:
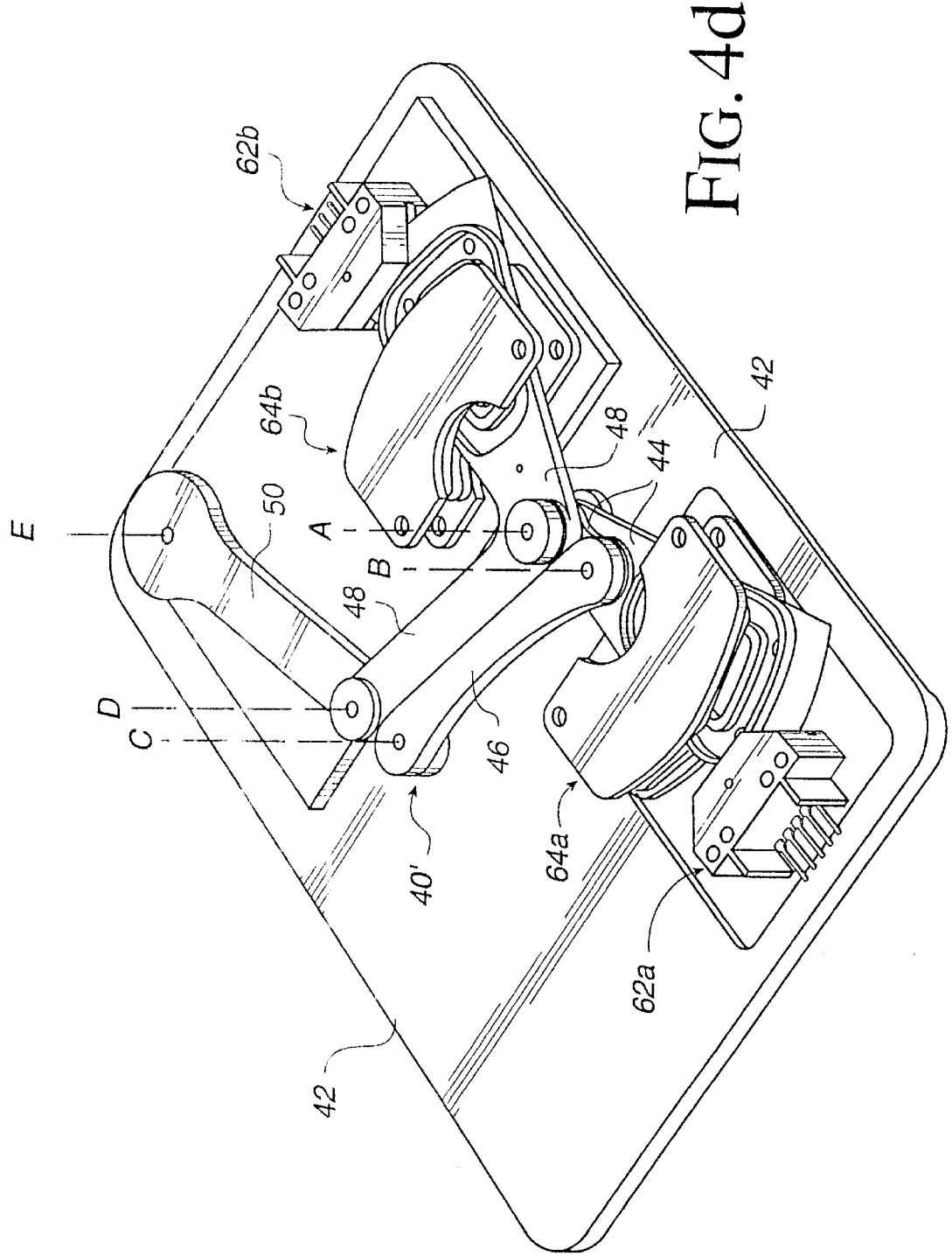
FIG. 4d is a perspective view of an alternate embodiment of the mouse interface of FIG. 2.
Figure 4E:
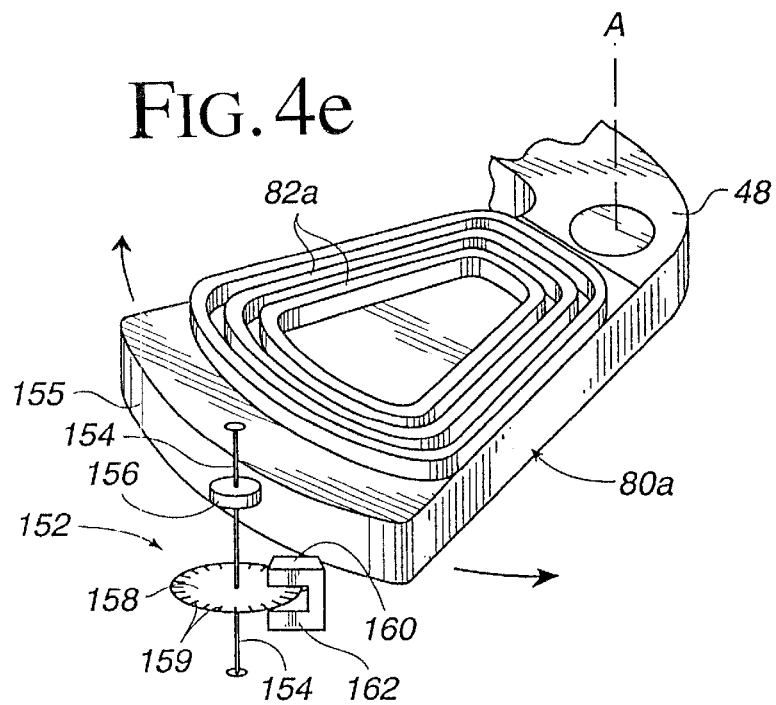
FIG. 4e is a perspective view of an alternate sensor having a friction wheel.

FIG. 4e is a diagrammatic illustration showing an alternate embodiment including rotary sensor 152 with a friction wheel. FIG. 4e shows portion 80a of member 48, which rotates about axis A. Instead of optical encoder sensor 64a, rotary sensor 152 can be used, which includes a grounded shaft 154, a roller 156, an encoder wheel 158, an emitter 160, and a detector 162. Roller 156 is preferably made of a material having high friction and is rigidly coupled to shaft 154 such that the surface of the roller 156 frictionally contacts the circular edge 155 of member 48. When member 48 rotates about axis A, roller 156 rotates shaft 154 about an axis extending through the shaft. Encoder wheel 158 is rigidly coupled to shaft 154 offset from the edge 155 of the member 48 and rotates when shaft 154 rotates. Included on encoder wheel 158 are marks 159 spaced equally around the perimeter of the encoder wheel. The edge of the encoder wheel passes between grounded emitter 160 and grounded sensor 162. Similar to the optical encoder embodiment described above, the encoder wheel can be made transparent, so that a beam emitted from emitter 160 is blocked from reaching detector 162 only when a mark 159 passes between the emitter and detector. Thus, detector 162 may send a signal or a count indicating how many marks pass by the detector. From this information, the position of the member 48 can be derived. Alternatively, the encoder wheel 158 may be made opaque, while marks 159 are notches cut out of the wheel 158 that allow the beam from the emitter to pass through and be detected by detector 162.

The embodiment of FIG. 4e is advantageous in that the marks 159 need not be as closely spaced as the marks 98 of the embodiment of FIG. 4c, since several rotations of encoder wheel 158 are completed for the range of motion of member 48 about axis A. This gearing up of the sensor resolution allows a less accurate, and less costly procedure, in producing the sensor. A disadvantage of this embodiment is that more moving parts are required, and the friction between roller 156 and edge 155 can wear down over time, causing slippage and inaccurate position detection.

Figure 4F:
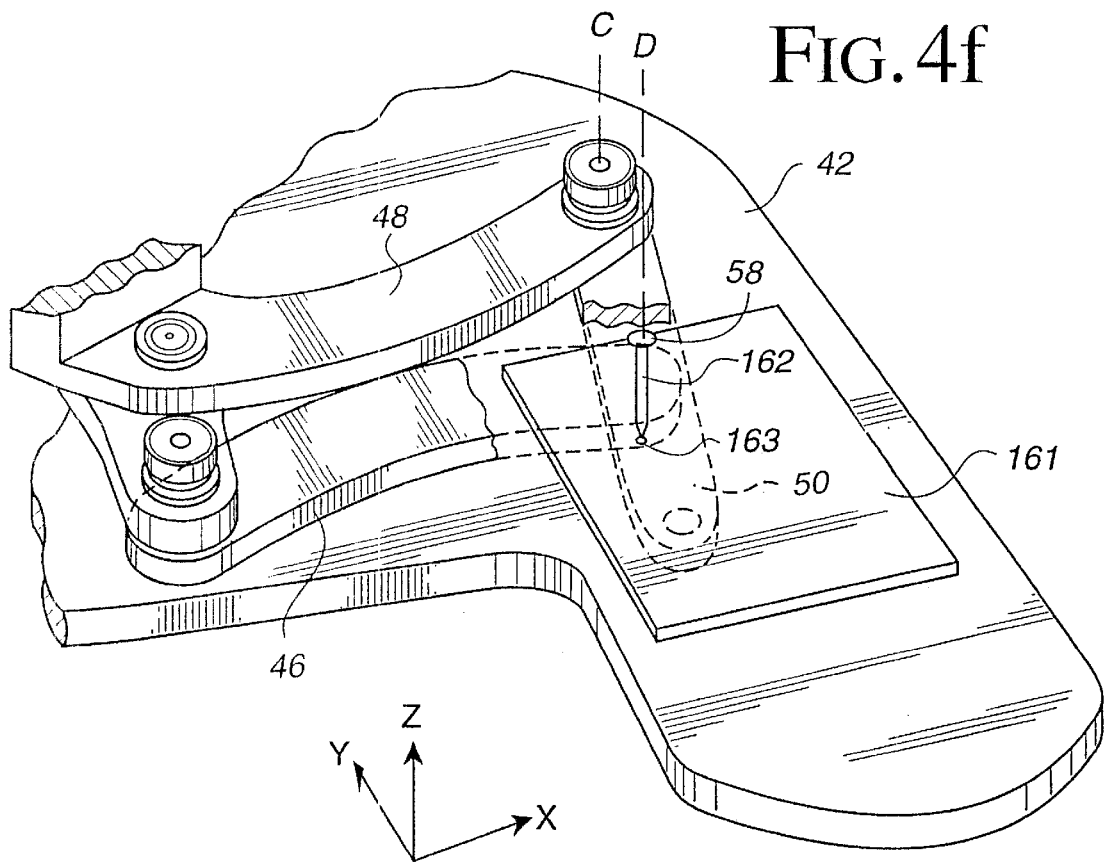
FIG. 4f is a perspective view of an alternate sensor having a planar sensor pad.

FIG. 4f is a perspective view of another alternate embodiment of a sensing system including a planar sensor 162.

Sensor 162 includes a planar sensor or "touch pad" 161 having rectangular sensing area and a pointer 162. Planar sensor 161 is preferably positioned somewhere beneath linkage 40; it is shown approximately at the position of opening 76 in FIG. 4f, but can be provided in other positions as well. Pointer 162 is coupled to bearing 58 at axis D and extends down to contact the tablet 161, and can be a plastic or metal nub, for example. Pointer 162 can also be placed at other bearings or positions of the linkage in other embodiments. The planar sensor 161 can also be placed within opening 76 so that pointer 162 acts as guide pin 78.

Planar sensor 161 is functional to detect the x and y coordinates of the tip 163 of pointer 162 on the tablet. Thus, as the mouse 12 is moved in its planar workspace, pointer 162 is moved to different locations on planar sensor 161. The x-y position of the local frame 30 on planar sensor 161 is transformed to the host frame 28 and the user controlled graphical object is displayed accordingly.

In the preferred embodiment, planar sensor 161 can also sense the pressure of tip 163 on the tablet, i.e., in the z-direction. For example, the Versapoint Semiconductive Touch Pad from Interlink is a suitable planar sensor that detects the x-y position as well as pressure or force in the z-direction. The pressure information can be useful in some embodiments for a variety of purposes. A first use is for a safety switch. The pressure information can be used to determine whether the user is currently placing weight on the user object. If the user is not placing weight, then the actuators can be deactivated for safety reasons, as described below with reference to FIG. 7b. A second use is for the indexing function, described below with reference to FIG. 7c. Both these functions might be performed only if the detected pressure in the z-direction is above or below a predetermined threshold (where different thresholds can be used for safety switch and indexing, if desired).

A third use is to use the pressure information to modify the output forces on user object 12. One use of pressure information is to control a friction force on the user object felt by the user. For example, if the user moves a controlled cursor over a frictional region, the force opposing movement across the region is output on the user object. If the pressure information in the z-axis is known from planar sensor 161, this pressure information can help determine the magnitude of simulated friction the user experiences as the cursor moves across the region. This is because friction in a lateral direction is a function of the force normal to the surface, which is the force in the z-direction from the user. If the user is exerting a large amount of pressure down on the user object, then a large friction force is felt, and vice versa, as if a real object were being scraped along the surface. This feature can be especially useful in drawing programs, where the amount of control in moving a virtual pen tip can be greatly enhanced if the user is able to input pressure information in the z-direction and control the amount of friction on the pen tip as it draws on the screen. Thus, pressure information in the z-axis can enhance the realism of force sensations output by the interface device 104.

The pressure information can also be used to control a damping force. A damping force is typically provided as a force proportional to velocity of the user object, where a coefficient of damping b is a proportionality constant. The damping coefficient can be modulated based on the sensed z-axis force exerted by the user, so that the experienced damping force is based on the velocity of the user object in the x-y plane as well as the force on the user object in the z-direction, where a larger z-axis force provides a larger damping coefficient and thus a larger damping force. The pressure information can also be used to control a texture force. One way to provide texture forces is to spatially vary a damping force, i.e., a damping force that varies on and off according to user object position, such as a series of bumps. The damping coefficient b can be varied to create the texture effect, where b is made high, then low, then high, etc. If pressure in the z-axis is available, the damping coefficients can be all globally increased or decreased by the same amount based on the amount of pressure. This causes a high pressure in the z-axis to provide a stronger texture force, and vice-versa. Texture can also be based on stiffness (k) as in a spring; the stiffness can be globally varied based on pressure information as with the damping texture force. Other types of forces may also be enhanced or modified if such pressure information is known.

In yet other embodiments, lateral effect photo diode sensors can be used in the mouse interface system 10. For example, such a photo diode sensor can include a rectangular or other-shaped detector positioned in place of the detector or emitter of sensors 62. A beam emitter that is coupled to ground member 42 or to grounded surface 34 can emit a beam of electromagnetic radiation which impinges on the detector. The position of the detector, and thus the rotating member, is known from the position of the beam on the detector area. The detector can be positioned on other areas or components of the linkage 40 in other embodiments. In other embodiments, the detector can be coupled to ground and the emitter can be coupled to the moving member (as in FIGS. 4i and 4j below).

FIGS. 4g1 and 4g2 are perspective and top plan views, respectively, showing a different lateral effect diode sensor 166 including a light pipe. A stationary emitter (e.g., a light emitting diode or LED) 168 positioned on ground member 42 or other grounded surface 34 emits a beam of electromagnetic energy. A light pipe 170 is a rigid member having a solid, transparent interior and two ends 171 and 172. End 171 is positioned over emitter 168 such that the emitted beam travels into the pipe 170. The beam travels through the light pipe and stays inside the pipe due to the index of refraction of the pipe material and angle of incidence of the beam, as shown by dashed line 173; the operation of light pipes is well known to those skilled in the art. The beam is reflected of 45-degree angled surfaces in the pipe and directed out of opening 172. Beam 174 is shown as a long narrow beam in FIG. 4g1, but can alternatively be provided as a circular or other shaped beam. The beam 174 is directed onto a detector 176, which is preferably a photo sensitive diode or similar detector, and is grounded similarly to emitter 168. Emitter 168 and detector 176 are preferably provided on the same grounded printed circuit board for a low cost embodiment. The beam 174 can cover a wider area than the detection area 178 of the detector 176, as shown. The detector outputs an electrical signal indicating the location of the beam on the area 178, as is well known to those skilled in the art.

In the described embodiment, light pipe 170 is rigidly coupled to a moving member, such as member 44 or member 48, at member 180. The light pipe is rotatable about axis $F_1$, which in this embodiment is not aligned with the emitter 168. Axis $F_1$ can be any of the axes of rotation of the members of linkage 40 or 40', including axes A, B, C, or D. Alternatively, the light pipe 166 can be placed over member 48 so that openings 171 and 172 are on either side of the member 48 and axis F1 is axis A. When the coupled member moves about axis $F_1$, the light pipe also rotates about axis $F_1$. The beam 174 on detector 176 thus moves as well and the rotated position of the member can be determined by the detected position of the beam on the detector. In one embodiment, the light pipe moves about 15 degrees in either direction about axis $F_1$ (depending on the movement range of the member to which it is coupled). The wide-mouthed shape of opening 171 allows the emitted beam 174 to be transmitted through the pipe regardless of the pipe's position over the emitter. A fiber optic cable or flexible pipe can also be used in other embodiments for light pipe 170. One advantage to this sensor embodiment is that both emitter and detector are grounded, thus greatly simplifying the assembly and reducing cost of the device since no wires need be routed to an emitter or detector positioned on a moving member of the linkage. Another embodiment of a sensor using a lateral effect photo diode is disclosed in patent application Ser. No. 08/560,091.

FIGS. 4h1 and 4h2 are perspective and top plan views, respectively, of an alternate embodiment 182 of the light pipe sensor of FIGS. 4g1 and 4g2. Sensor 182 includes an emitter 184, a light pipe 186, and a detector 188 which operate substantially the same as these components in FIG. 4g1 and 4g2. A centroid location 191 of the beam can be detected by the detector 188. Light pipe 186 is rigidly coupled to a moving member such as member 44 or 48 and may rotate about axis $F_2$ with the coupled member, where axis $F_2$ may be any of the axes of rotation of the linkage 40 or 40'. In this embodiment, however, the beam is emitted from emitter 184 coaxially with the axis of rotation $F_2$ of the light pipe. Since the light pipe may rotate about the axis of the emitted beam, the opening 190 of light pipe 186 can be made narrower than the wide opening 171 of the light pipe 170. In addition, this configuration has the advantage over light pipe 170 in that the beam 192 directed at detector 188 is more uniform throughout the range of motion of the pipe, since the emitter source 184 does not change its position relative to the opening 190 of the pipe.

Figure 4I:
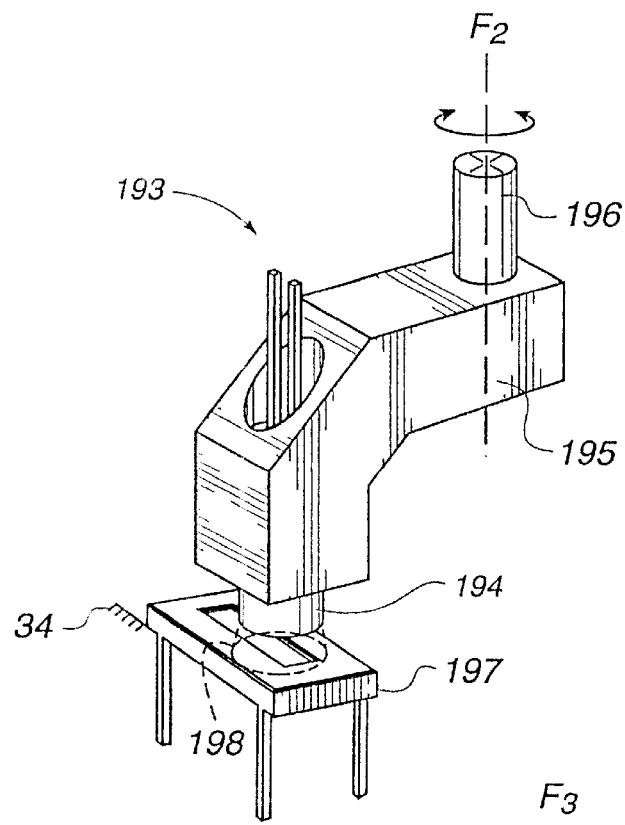
FIGS. 4i and 4j are perspective views of alternate sensors including an emitter and detector.

FIG. 4i is a perspective view of another alternate embodiment of a sensor 193 for use with the present invention. An emitter 194 is mounted to a rotating arm 195 that is in turn rigidly coupled to a moving member such as member 44 or 48 by a coupling 196. Rotating arm 195 thus rotates about an axis $F_3$ when the connected member of the linkage rotates, where axis $F_3$ is the axis of rotation of the connected member and may be any of the axes of rotation of the linkage 40 or 40'. In the embodiment shown, a directed beam 198 of electromagnetic energy is shaped substantially circular and is directed at a grounded detector 197 which is similar to the detectors described above. The directed beam thus sweeps over the detecting area of the detector 197 when the arm 195 and the connected member rotate, allowing the detector to sense the position of the member. The directed beam can be of other shapes in other embodiments. Rotating arm 195, in alternate embodiments, can be part of an existing member of the linkage 40 or 40', e.g. an extension of a member of the linkage rather than a separate component.

Figure 4J:
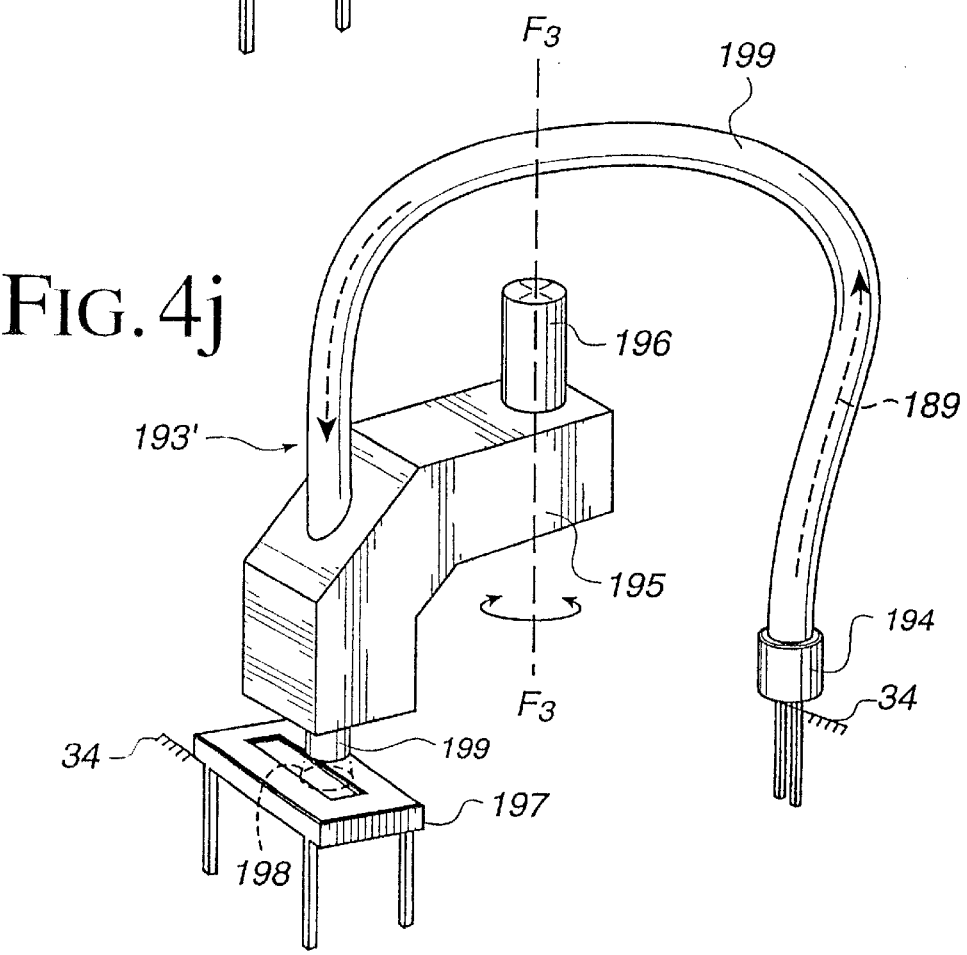

FIG. 4j is a perspective view of an alternate embodiment 193' of the sensor 193 of FIG. 4i. Embodiment 193' includes a rotating arm 195 and detector 197 as described in FIG. 4i. In addition, a flexible fiber optic cable 199 or similar flexible light guide is coupled between the emitter 194 and the arm 195. Fiber optic cable 199 guides a light beam 189 from emitter 194 and along the cable's length, where the transmission of light through such a cable is well known to those skilled in the art. The beam is guided to arm 195, where the beam 189 is directed onto detector 197 as in FIG. 4i. The cable 199 may flex as the arm 195 rotates about axis $F_3$. This embodiment allows the emitter 194 to be grounded as well as the detector 197, thus simplifying assembly and reducing the manufacturing cost of the device.

Figure 5A:
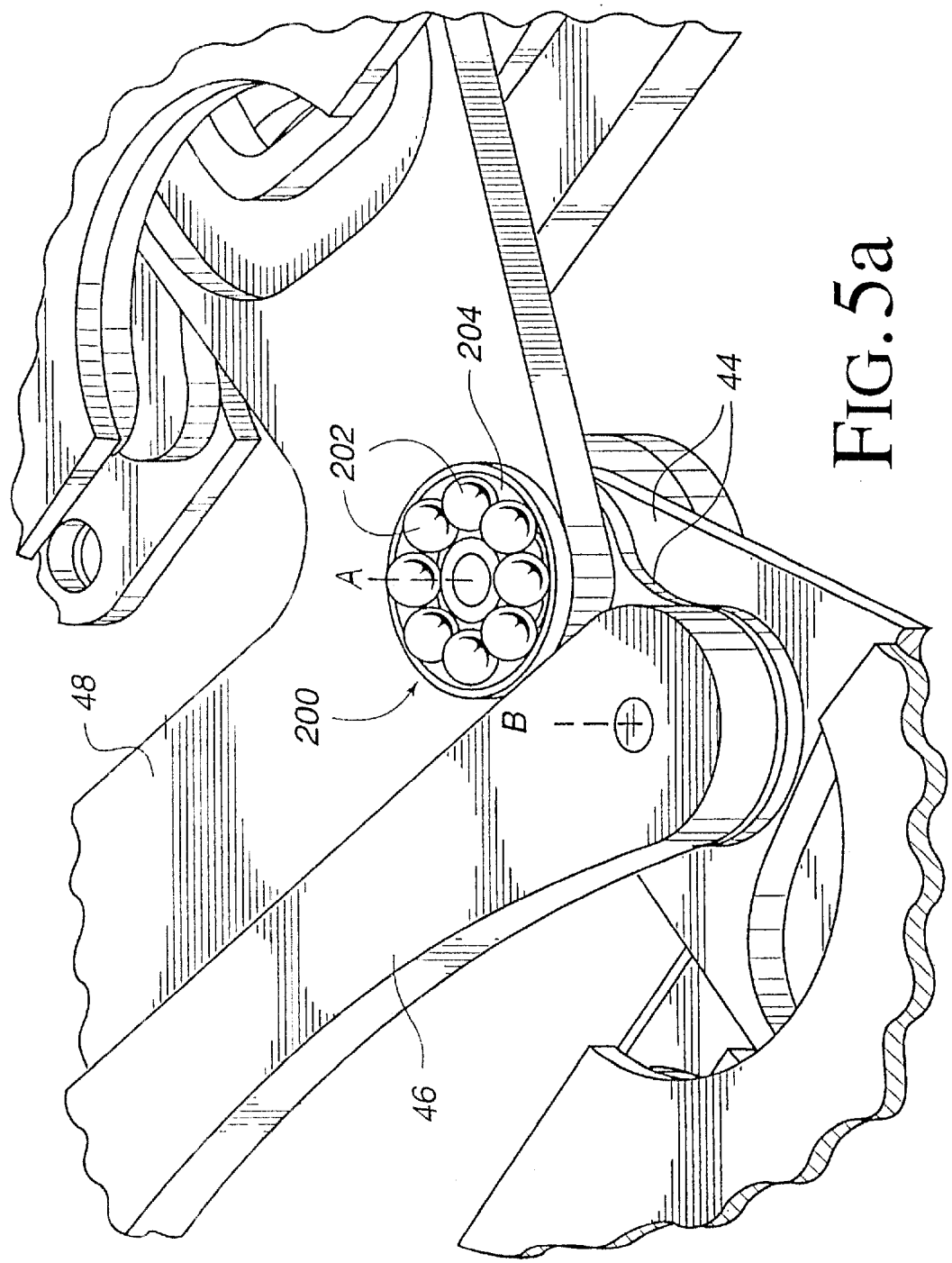
FIGS. 5a and 5b are perspective and side elevational views, respectively, of a ball bearing assembly suitable for use in the mouse interface of the present invention.
Figure 5B:
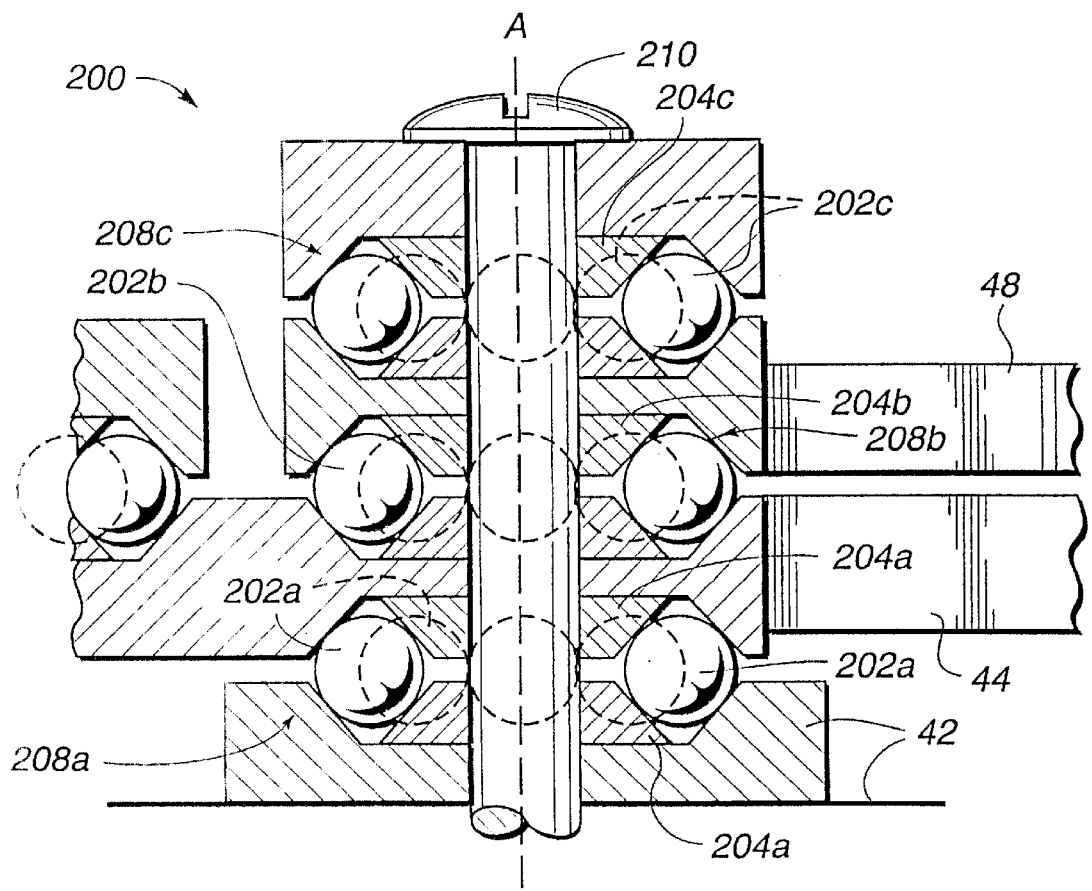

FIG. 5a is a perspective view and FIG. 5b is a side elevational view of one embodiment of a ball bearing assembly 200 suitable for use for rotatably connecting the members of linkage 40 or 40' of the present invention. The linkage 40' of the alternate embodiment of FIG. 4d is shown in FIG. 5a; however, the bearing assembly 200 can also be used in the embodiment of FIG. 2. The ball bearing assembly 200 includes a row 206 of individual balls 202 that ride in V-shaped grooves 204 (bearing races) which are an integral part of each member. FIG. 5b shows a side elevational view of one implementation of the bearing assembly 200 about the grounded axis A of the alternate embodiment of FIG. 4d. This bearing assembly includes several layers 208 of balls 202, where a first layer 208a of balls 202a is positioned in a ring within V-shaped groove 204a between the ground member 42 and the base member 44. On the base member 44 is positioned layer 208b of balls 202b in a ring within V-shaped groove 204b. Base member 48 is positioned over layer 208b, and a top cap layer 208c of balls 202c within V-shaped groove 204c is positioned over the base member 48. The entire bearing assembly 200 is then preloaded with a screw 210 or spring loading mechanism to keep all the components of the bearing assembly tightly coupled together. Advantages of the bearing assembly 200 include low cost of manufacture since the parts are widely available and inexpensive, and high stiffness and compactness.

Figure 5C:
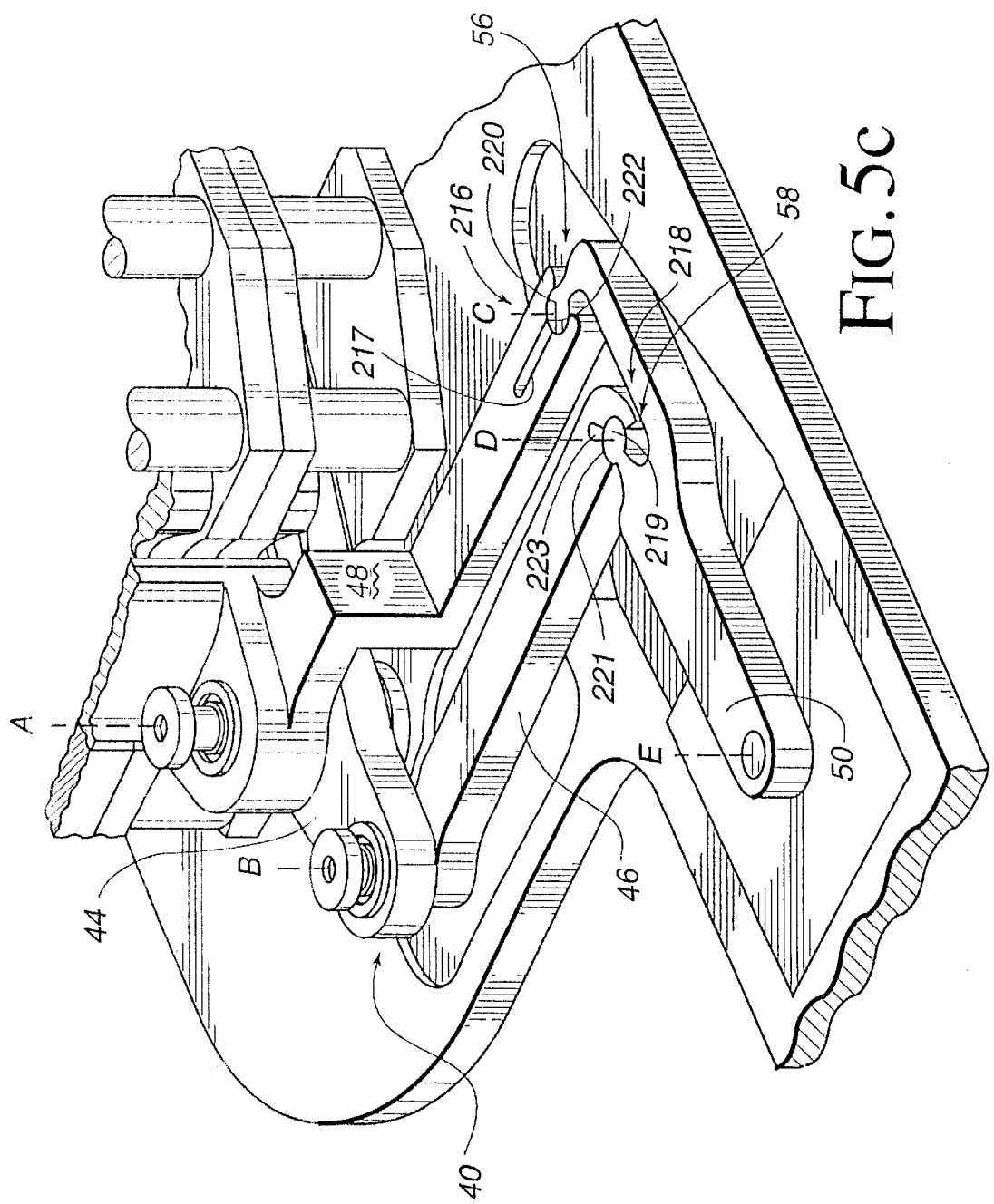
FIG. 5c is a snap bearing of the present invention suitable for use with the mouse interface of the present invention.

FIG. 5c is a perspective view of an alternate embodiment for bearings of the linkage 40 or 40'. In the described embodiment of FIG. 5c, snap bearing 216 is provided for bearing 56, and snap bearing 218 is provided for bearing 58. One part of bearing 216 is a cylindrical boss 220 included as part of member 50, which mates with cylindrical cavity 222 included in member 48. A slot 217 in member 48 which extends from the cylindrical cavity 222 creates a spring that allows the sides of the cavity 222 to grab the boss 220 with a predetermined amount of force. The boss 220 can be made of a slippery plastic material such as Delrin, while the cavities can be made of metal as is member 48. Likewise, one part of bearing 218 is a cylindrical boss 219 included as part of member 50 which mates with cylindrical cavity 221 included in member 46. A slot 223 in member 446 extends from the cavity 221 and creates a spring force that grabs boss 219 with a predetermined amount of force. In addition, upper and lower flanges, or other devices, can be provided on the cylindrical bosses 220 and 219 to prevent the elements of bearings 216 and 218 from sliding apart along axes C and D, i.e., to keep the members of the linkage substantially in the same plane. Similar bearings to 216 and 218 can be used for the other bearings of linkage 40 or 40'.

The bearings 216 and 218 use the natural springiness (elasticity) of elements 46 and 48 to hold the elements 48, 50, and 46 together, and thus can provide a connection having close to zero play due to the created spring force. Preferably, these bearings can be simply snapped together to provide a low cost, easy-to-assemble linkage 40 or 40'.

FIGS. 5d1 and 5d2 are perspective views of an alternate embodiment 224 of the snap bearings 216 and 218 of FIG. 5c. As shown in FIG. 5d1, bearing 224 includes a fork 225 provided, in the example shown, on member 48 (the bearing 224 can be provided on other members of linkage 40 or 40' as well). Fork 225 includes two prongs 226 that each include a cavity 227 for receiving a corresponding assembly of bearing 224 (not shown in FIG. 5d1). Like the snap bearings 216 and 218 of FIG. 5c, a slot 228 extends from each of the cavities 227 on the prongs 226. In FIG. 5d1, bearing 58 on member 46 is a standard bearing having two prongs for holding a corresponding portion (not shown) of a bearing on the attached member.

In FIG. 5d2, member 50 has been attached to members 46 and 48. Bearing 224 couples member 48 with member 50. A bearing assembly 229 of member 50 includes two cylindrical bosses 230 at either end which "snap" into (mate with) the prongs 226 of the fork 225 on member 48 and is rigidly held by a predetermined amount of spring force caused by slot 228 and the elasticity of the prong material. Member 50 is attached to member 46 using a standard bearing 58; in other embodiments, bearing 58 can be a bearing similar to bearing 224. Bearing 224 can be made of similar materials as described in FIG. 5c.

Figure 5E:
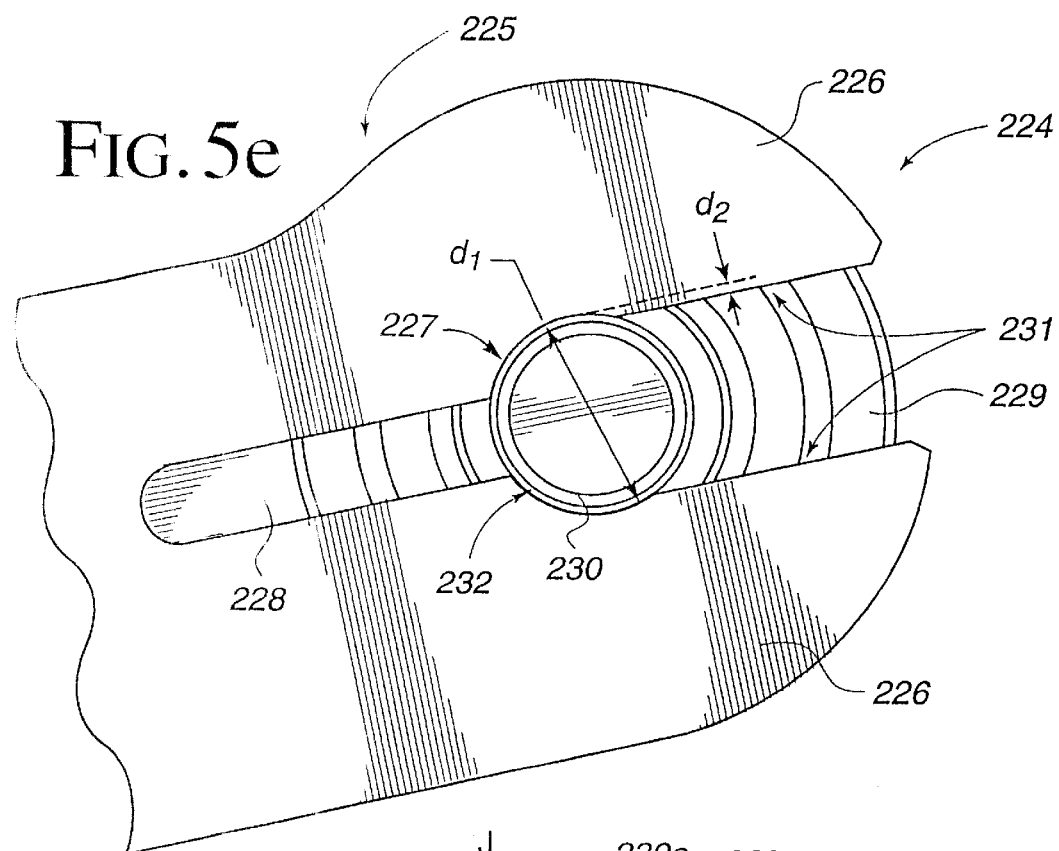
FIG. 5e is a top plan view of the snap bearing of FIGS. 5d1 and 5d2.

FIG. 5e is a top plan view of bearing 224 where assembly 229 is mated with fork 225. As shown, the cylindrical cavity 227 preferably has a diameter d1 to which the boss 230 of assembly 229 is matched in size. The forward portion 231 of cavity 227 preferably is narrower than the diameter $d_1$ of the cavity 227 by an amount $d_2$ on each side of the portion 231. This allows the boss 230 of the assembly 229 to fit more snugly in the mating portion 232 of the cavity and holds the boss 230 in place within the mating portion of the cavity 227.

Figure 5F:
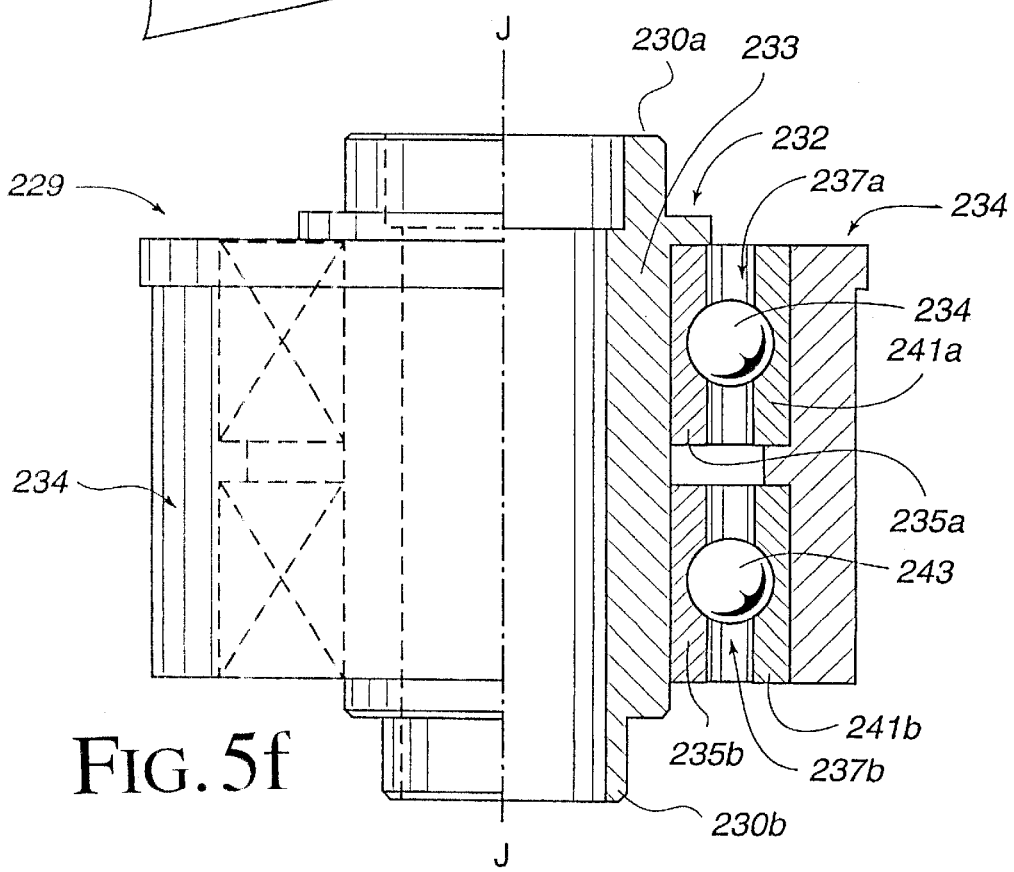
FIG. 5f is a side partial sectional view of the rotating bearing assembly of the snap bearing of FIGS. 5d1 and 5d2.

FIG. 5f is a side partial sectional view of bearing assembly 229 of the bearing 224. Assembly 229 preferably includes a bearing 232 and a bearing 234 which may rotate with respect to each other about axis J (which may be any of the axes A, B, C, D, or E of the linkage 40 or 40'). Bearing 232 includes the boss 230 which is coupled to inner shaft 233, which in turn is coupled to inner races 235a and 235b of ball bearing grooves 237a and 237b, respectively. Bearing 234 includes outer housing 239 which is coupled to outer races 241a and 241b of ball bearing grooves 237a and 237b, respectively. A number of balls 243 are provided in grooves 237a and 237b and operate as a standard ball bearing or as bearing 200 of FIG. 5a, i.e., balls 243 move in grooves 237a and 237b (or the races 235 and 241 move relative to the balls) as the two bearings 232 and 234 rotate relative to each other. Assembly 229 is preloaded with adhesive or other fasteners to create a tight assembly. Thus, in the example of FIGS. 5d1 and 5d2, the member 48 is coupled to the boss 230 and inner races 235a and 235b through fork 225, while the member 50 is coupled to the outer housing 234 and outer races 241a and 241b, thus allowing member 48 and member 50 to rotate about axis C relative to each other. Bearing 224 provides low friction bearing and has very little play.

Bearing 224 is also well-suited to be used at axis A of the linkage 40 or 40', where members 44 and 48 are both rotatably coupled to ground member 42 or ground 34 in the described embodiment such that member 48 is positioned above member 44. Bearing 224 can be stacked on another bearing 224 at axis A, where the lower boss 230a of the upper assembly 229 attached to member 48 can be inserted into the upper boss 230b of the lower assembly 229 attached to member 44, providing a rigid inner shaft between both assemblies 229 concentric around axis A. An empty shaft can be provided through the assemblies 229 to allow a screw or other fastener to attach the assemblies 229 to ground member 42.

FIG. 5g1 is a perspective view of another alternate bearing 234 which can be used for some or all of the bearings of linkage 40 or 40'. For example, the bearing 234 can be used for bearing 56 or 58 of the embodiment of FIG. 2. Bearing 234 includes a V-shaped notch 236 which mates with a V-shaped edge 238. The angle between the sides of notch 236 is greater than the angle between the sides of edge 238 by an amount greater than or equal to the desired range of angular motion provided by the bearing 234. In addition, a web element 240 is provided in the center of notch 236 which corresponds and mates with a notch 242 in V-shaped edge 238. The web element 240 and notch 242 prevent the elements of the linkage connected by bearing 234 from moving out of substantially planar relation to each other. FIG. 5g2 shows the bearing 234 when the elements of the linkage have been connected together. The bearing provides smooth rotational motion of the elements with respect to each other about axis G with very little friction. The bearing 234 can be held together, for example, by a spring element 244 (shown symbolically) connected between two posts 246 on the connected elements. Other types of connections can preload the bearing to keep its parts together in other embodiments.

Figure 6:
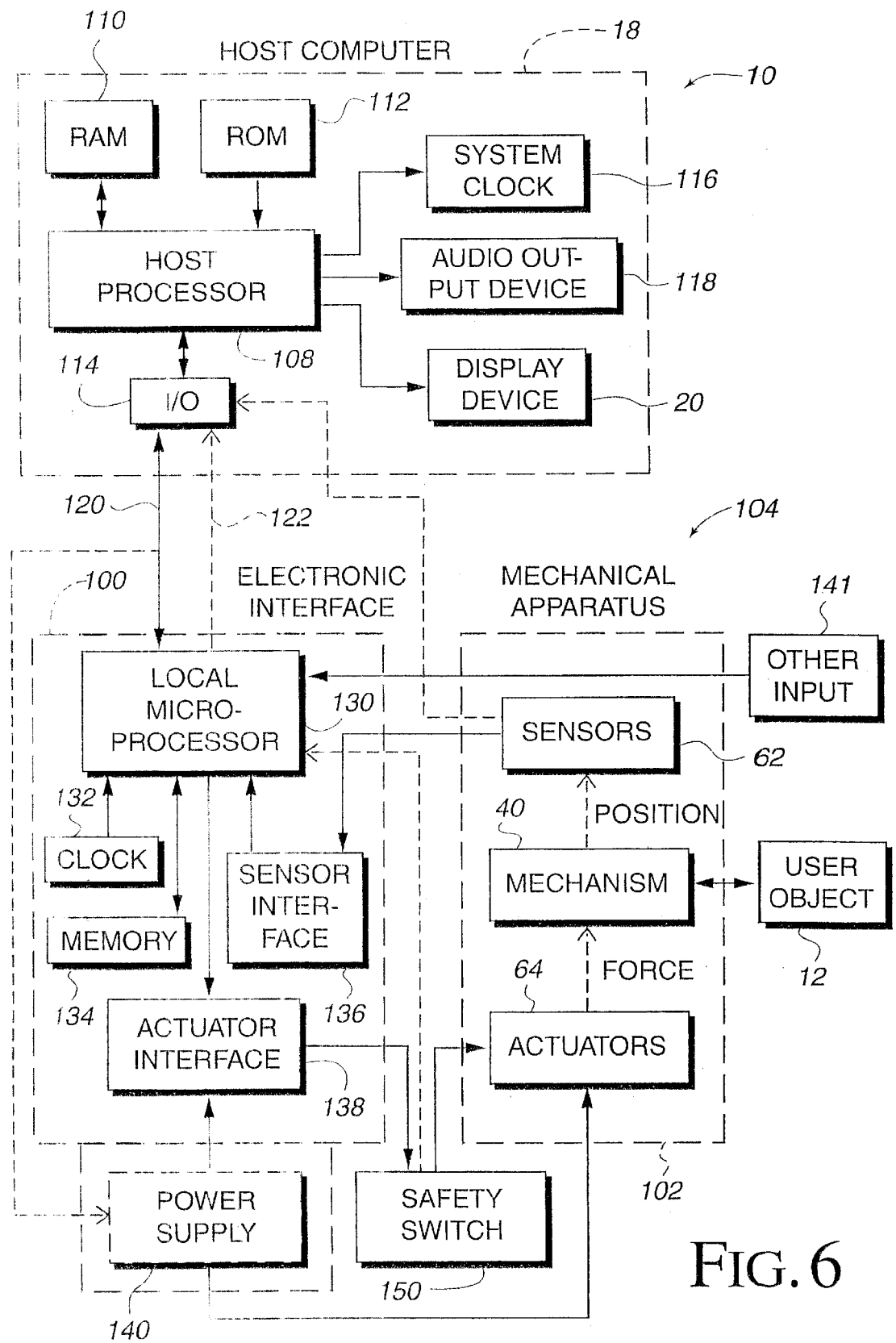
FIG. 6 is a block diagram of the system of FIG. 1 for controlling a force feedback interface device of the present invention.

FIG. 6 is a block diagram illustrating the electronic portion of interface 14 and host computer 18 suitable for use with the present invention. Mouse interface system 10 includes a host computer 18, electronic interface 100, mechanical apparatus 102, and mouse or other user object 12. Electronic interface 100, mechanical apparatus 102, and mouse 12 can also collectively be considered a "force feedback interface device" 104 that is coupled to the host computer. A similar system is described in detail in co-pending patent application Ser. No. 08/566,282, now Pat. No. 5,734,373, which is hereby incorporated by reference herein in its entirety.

As explained with reference to FIG. 1, computer 18 is preferably a personal computer, workstation, video game console, or other computing or display device. Host computer system 18 commonly includes a host microprocessor 108, random access memory (RAM) 110, read-only memory (ROM) 112, input/output (I/O) electronics 114, a clock 116, a display device 20, and an audio output device 118. Host microprocessor 108 can include a variety of available microprocessors from Intel, AMD, Motorola, or other manufacturers. Microprocessor 108 can be single microprocessor chip, or can include multiple primary and/or co-processors. Microprocessor 108 preferably retrieves and stores instructions and other necessary data from RAM 110 and ROM 112 as is well known to those skilled in the art. In the described embodiment, host computer system 18 can receive sensor data or a sensor signal via a bus 120 from sensors of system 10 and other information. Microprocessor 108 can receive data from bus 120 using I/O electronics 114, and can use I/O electronics to control other peripheral devices. Host computer system 18 can also output commands to interface device 104 via bus 120 to cause force feedback for the interface system 10.

Clock 116 is a standard clock crystal or equivalent component used by host computer 18 to provide timing to electrical signals used by host microprocessor 108 and other components of the computer system 18. Clock 116 is accessed by host computer 18 in the control process of the present invention to provide timing information that may be necessary in determining force or position, e.g., calculating a velocity or acceleration from position values.

Display device 20 is described with reference to FIG. 1. Audio output device 118, such as speakers, can be coupled to host microprocessor 108 via amplifiers, filters, and other circuitry well known to those skilled in the art. Host processor 108 outputs signals to speakers 118 to provide sound output to the user when an "audio event" occurs during the implementation of the host application program. Other types of peripherals can also be coupled to host processor 108, such as storage devices (hard disk drive, CD ROM drive, floppy disk drive, etc.), printers, and other input and output devices.

Electronic interface 100 is coupled to host computer system 18 by a bi-directional bus 120. The bi-directional bus sends signals in either direction between host computer system 18 and the interface device 104. Bus 120 can be a serial interface bus providing data according to a serial communication protocol, a parallel bus using a parallel protocol, or other types of buses. An interface port of host computer system 18, such as an RS232 serial interface port, connects bus 120 to host computer system 18. In another embodiment, an additional bus 122 can be included to communicate between host computer system 18 and interface device 13. Bus 122 can be coupled to a second port of the host computer system, such as a "game port", such that two buses 120 and 122 are used simultaneously to provide an increased data bandwidth.

One preferred serial interface bus used in the present invention is the Universal Serial Bus (USB). The USB standard provides a relatively high speed serial interface that can provide force feedback signals in the present invention with a high degree of realism. USB can also source power to drive actuators 64 and other devices of the present invention. Since each device that accesses the USB is assigned a unique USB address by the host computer, this allows multiple devices to share the same bus. In addition, the USB standard includes timing data that is encoded along with differential data.

Electronic interface 100 includes a local microprocessor 130, local clock 132, local memory 134, sensor interface 136, and actuator interface 138. Interface 100 may also include additional electronic components for communicating via standard protocols on buses 120 and 122. In various embodiments, electronic interface 100 can be included in mechanical apparatus 102, in host computer 18, or in its own separate housing. Different components of interface 100 can be included in apparatus 102 or host computer 18 if desired.

Local microprocessor 130 preferably coupled to bus 120 and may be closely linked to mechanical apparatus 102 to allow quick communication with other components of the interface device. Processor 130 is considered "local" to interface device 104, where "local" herein refers to processor 130 being a separate microprocessor from any processors 108 in host computer 18. "Local" also preferably refers to processor 130 being dedicated to force feedback and sensor I/O of the interface system 10, and being closely coupled to sensors and actuators of the mechanical apparatus 102, such as within the housing of or in a housing coupled closely to apparatus 102. Microprocessor 130 can be provided with software instructions to wait for commands or requests from computer host 18, parse/decode the command or request, and handle/control input and output signals according to the command or request. In addition, processor 130 preferably operates independently of host computer 18 by reading sensor signals and calculating appropriate forces from those sensor signals, time signals, and force processes selected in accordance with a host command, and output appropriate control signals to the actuators. Suitable microprocessors for use as local microprocessor 200 include the MC68HC711E9 by Motorola and the PIC16C74 by Microchip, for example. Microprocessor 130 can include one microprocessor chip, or multiple processors and/or co-processor chips. In other embodiments, microprocessor 130 can include digital signal processor (DSP) functionality.

For example, in one host-controlled embodiment that utilizes microprocessor 130, host computer 18 can provide low-level force commands over bus 120, which microprocessor 130 directly transmits to the actuators. In a different local control embodiment, host computer system 18 provides high level supervisory commands to microprocessor 130 over bus 120, and microprocessor 130 manages low level force control loops to sensors and actuators in accordance with the high level commands and independently of the host computer 18. In the local control, embodiment, the microprocessor 130 can process inputted sensor signals to determine appropriate output actuator signals by following the instructions of a "force process" that may be stored in local memory and includes calculation instructions, formulas, force magnitudes, or other data. The force process can command distinct force sensations, such as vibrations, textures, jolts, or even simulated interactions between displayed objects. An "enclosure" host command can also be provided, which causes the microprocessor to define a box-like enclosure in a graphical environment, where the enclosure has sides characterized by wall and texture forces. For example, an enclosure command can include parameters to specify the size and location of the enclosure in the graphical environment, the wall stiffness and width, surface texture and friction of the wall, clipping, force characteristics of the interior region of the enclosure, scroll surfaces, and the speed of the user object necessary to engage the forces of the enclosure. The microprocessor may locally determine whether the cursor is inside or outside the enclosure, and characteristics of the enclosure are specified in the command as parameters. The host can send the local processor a spatial layout of objects in the graphical environment so that the microprocessor has a mapping of locations of graphical objects like enclosures and can determine interactions with the cursor locally. Force feedback used in graphical environments is described in greater detail in co-pending patent application Ser. Nos. 08/571,606, 08/756,745, and 08/879,296, entitled, "Graphical Click Surfaces for Force Feedback Applications", by Rosenberg et al., filed Jun. 18, 1997, all of which are incorporated by reference herein.

Sensor signals used by microprocessor 130 are also reported to host computer system 18, which updates a host application program and outputs force control signals as appropriate. For example, if the user moves mouse 12, the computer system 18 receives position and/or other signals indicating this movement and can move a displayed cursor in response. These embodiments are described in greater detail in co-pending applications Ser. No. 08/534,791 (now Pat. No. 5,739,811) and Ser. No. 08/566,282. In an alternate embodiment, no local microprocessor 130 is included in interface system 10, and host computer 18 directly controls and processes all signals to and from the interface 100 and mechanical interface 102.

A local clock 132 can be coupled to the microprocessor 130 to provide timing data, similar to system clock 116 of host computer 18; the timing data might be required, for example, to compute forces output by actuators 64 (e.g., forces dependent on calculated velocities or other time dependent factors). In alternate embodiments using the USB communication interface, timing data for microprocessor 130 can be retrieved from the USB interface.

Local memory 134, such as RAM and/or ROM, is preferably coupled to microprocessor 130 in interface 100 to store instructions for microprocessor 130 and store temporary and other data. Microprocessor 130 may also store calibration parameters in a local memory 134 such as an EEPROM. As described above, link or member lengths or manufacturing variations in link lengths can be stored. Variations in coil winding or magnet strength can also be stored. If analog sensors are used, adjustments to compensate for sensor variations can be included, e.g. implemented as a look up table for sensor variation over the user object workspace. Memory 134 may be used to store the state of the force feedback device, including a reference position, current control mode or configuration, etc.

Sensor interface 136 may optionally be included in electronic interface 100 convert sensor signals to signals that can be interpreted by the microprocessor 130 and/or host computer system 18. For example, sensor interface 136 can receive signals from a digital sensor such as an encoder and convert the signals into a digital binary number representing the position of a member or component of mechanical apparatus 14. An analog to digital converter (ADC) in sensor interface 136 can convert a received analog signal to a digital signal for microprocessor 130 and/or host computer 18. Such circuits, or equivalent circuits, are well known to those skilled in the art. Alternately, microprocessor 130 can perform these interface functions without the need for a separate sensor interface 136. Or, sensor signals from the sensors can be provided directly to host computer system 18, bypassing microprocessor 130 and sensor interface 136. Other types of interface circuitry 136 can also be used. For example, an electronic interface is described in U.S. Pat. No. 5,576,727, which is hereby incorporated by reference herein.

Actuator interface 138 can be optionally connected between the actuators 64 and microprocessor 130. Interface 138 converts signals from microprocessor 130 into signals appropriate to drive the actuators. Interface 138 can include power amplifiers, switches, digital to analog controllers (DACs), and other components. Such interfaces are well known to those skilled in the art. In alternate embodiments, interface 138 circuitry can be provided within microprocessor 130 or in the actuators.

In the described embodiment, power is supplied to the actuators 64 and any other components (as required) by the USB. Since the electromagnetic actuators of the described embodiment have a limited physical range and need only output about 3 ounces of force to create realistic force sensations on the user, very little power is needed. By drawing all of its required power directly off the USB bus, a large power supply need not be included in interface system 10 or as an external power adapter. For example, one way to draw additional power from the USB is to configure interface 100 and apparatus 102 to appear as more than one peripheral to host computer 18; for example, each provided degree of freedom of mouse 12 can be configured as a different peripheral and receive its own allocation of power. Alternatively, power from the USB can be stored and regulated by interface 100 or apparatus 102 and thus used when needed to drive actuators 64. For example, power can be stored over time and then immediately dissipated to provide a jolt force to the user object 12. A battery or a capacitor circuit, for example, can store energy and discharge or dissipate the energy when power is required by the system and/or when enough power has been stored. Alternatively, a power supply 140 can optionally be coupled to actuator interface 138 and/or actuators 64 to provide electrical power. Power supply 140 can be included within the housing of interface 100 or apparatus 102, or can be provided as a separate component, for example, connected by an electrical power cord. The power storage embodiment described above, using a battery or capacitor circuit, can also be used in non-USB embodiments to allow a smaller power supply 140 to be used.

Mechanical apparatus 102 is coupled to electronic interface 100 preferably includes sensors 62, actuators 64, and linkage 40. These components are described in detail above. Sensors 62 sense the position, motion, and/or other characteristics of mouse 12 along one or more degrees of freedom and provide signals to microprocessor 130 including information representative of those characteristics. Typically, a sensor 62 is provided for each degree of freedom along which mouse 12 can be moved, or, a single compound sensor can be used for multiple degrees of freedom. Example of sensors suitable for embodiments described herein are optical encoders, as described above. Linear optical encoders may similarly sense the change in position of mouse 12 along a linear degree of freedom. Alternatively, analog sensors such as potentiometers can be used. It is also possible to use non-contact sensors at different positions relative to mechanical apparatus 100, such as Hall effect magnetic sensors for detecting magnetic fields from objects, or an optical sensor such as a lateral effect photo diode having an emitter/detector pair. In addition, velocity sensors (e.g., tachometers) for measuring velocity of mouse 12 and/or acceleration sensors (e.g., accelerometers) for measuring acceleration of mouse 12 can be used. Furthermore, either relative or absolute sensors can be employed.

Actuators 64 transmit forces to mouse 12 in one or more directions along one or more degrees of freedom in response to signals output by microprocessor 130 and/or host computer 18, i.e., they are "computer controlled." Typically, an actuator 64 is provided for each degree of freedom along which forces are desired to be transmitted. Actuators 64 can include two types: active actuators and passive actuators. Active actuators include linear current control motors, stepper motors, pneumatic/hydraulic active actuators, a torquer (motor with limited angular range), a voice coil actuator as described in the embodiments above, and other types of actuators that transmit a force to an object. Passive actuators can also be used for actuators 64, such as magnetic particle brakes, friction brakes, or pneumatic/hydraulic passive actuators, and generate a damping resistance or friction in a degree of motion. For example, an electrorheological fluid can be used in a passive damper, which is a fluid that has a viscosity that can be changed by an electric field. Likewise, a magnetorheological fluid can be used in a passive damper, which is a fluid that has a viscosity that can be changed by a magnetic field (and typically requires less power than an electrorheological fluid). These types of dampers can be used instead of or in addition to other types of actuators in the mouse interface device. In yet other embodiments, passive damper elements can be provided on the bearings of apparatus 100 to remove energy from the system and intentionally increase the dynamic stability of the mechanical system. In addition, in voice coil embodiments, multiple wire coils can be provided, where some of the coils can be used to provide back EMF and damping forces. In some embodiments, all or some of sensors 62 and actuators 64 can be included together as a sensor/actuator pair transducer.

Mechanism 40 is preferably the five-member linkage 40 described above, but can also be one of several types of mechanisms. For example, mechanisms disclosed in co-pending patent applications Ser. Nos. 08/374,288 (now Pat. No. 5,731,804), 08/400,233 (now Pat. No. 5,767,839), 08/489,068 (now Pat. No. 5,721,566), 08/560,091 (now Pat. No. 5,805,140), 08/623,660 (now Pat. No. 5,691,898), 08/664,086, 08/709,012, and 08/736,161 (now Pat. No. 5,828,197), all incorporated by reference herein, can be included. Mouse 12 can alternatively be a puck, joystick, or other device or article coupled to linkage 40, as described above.

Other input devices 141 can optionally be included in system 10 and send input signals to microprocessor 130 and/or host computer 18. Such input devices can include buttons, such as buttons 15 on mouse 12, used to supplement the input from the user to a GUI, game, simulation, etc. Also, dials, switches, voice recognition hardware (with software implemented by host 18), or other input mechanisms can be used.

Safety or "deadman" switch 150 is preferably included in interface device to provide a mechanism to allow a user to override and deactivate actuators 64, or require a user to activate actuators 64, for safety reasons. Certain types of actuators, especially active actuators, can pose a safety issue for the user if the actuators unexpectedly move mouse 12 against the user with a strong force. In addition, if a failure in the system 10 occurs, the user may desire to quickly deactivate the actuators to avoid any injury. To provide this option, safety switch 150 is coupled to actuators 64. In the preferred embodiment, the user must continually activate or close safety switch 150 during manipulation of mouse 12 to activate the actuators 64. If, at any time, the safety switch is deactivated (opened), power is cut to actuators 64 (or the actuators are otherwise deactivated) as long as the safety switch is opened. For example, one embodiment of safety switch is a mechanical or optical switch located on mouse 12 or on a convenient surface of a housing 26. For example, when the user covers an optical safety switch with a hand or finger, the sensor of the switch is blocked from sensing ambient light, and the switch is closed. The actuators 64 thus will function as long as the user covers the switch. Other types of safety switches 150 can also be used, such as an electrostatic contact switch can be used to sense contact of the user. A preferred safety switch is described with reference to FIG. 7b. The safety switch can be provided between the actuator interface 138 and actuators 64 as shown in FIG. 6; or, the switch can be placed elsewhere. In some embodiments, the state of the safety switch is provided to the microprocessor 130 to provide further control over output forces. In addition, the state of the safety switch can be sent to the host 18, which can choose to stop sending force feedback commands if the safety switch is open. In yet other embodiments, a second switch can be provided to allow the user to turn off output forces of interface device 13 when desired, yet still operate the interface as an input device. The host 18 need not send force feedback commands when such a secondary switch has turned off forces.

In some embodiments of interface system 10, multiple mechanical apparatuses 102 and/or electronic interfaces 100 can be coupled to a single host computer system 18 through bus 120 (or multiple buses 120) so that multiple users can simultaneously interface with the host application program (in a multi-player game or simulation, for example). In addition, multiple players can interact in the host application program with multiple interface systems 10 using networked host computers 18, as is well known to those skilled in the art.

Figure 7A:
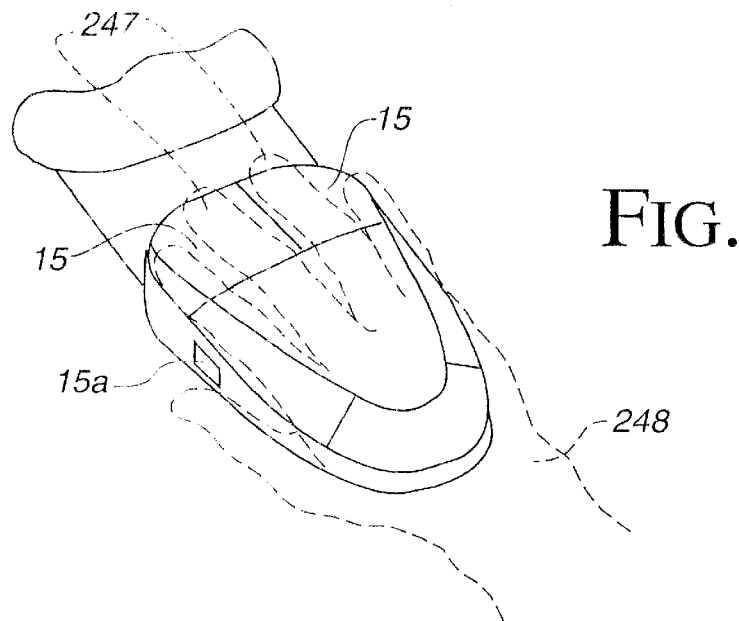
FIG. 7a is a perspective view of a mouse interface object for use with the interface system of FIG. 1.

FIG. 7a is a perspective view of a mouse 12 suitable for use with the present invention. Mouse 12 can be shaped to comfortably fit a user's fingers and/or hand when the user manipulates the mouse, e.g., mouse 12 can be shaped much like a standard mouse used for inputting information to a computer system. The mouse 12 can take a variety of shapes in different embodiments, from a small knob or sphere to a grip having indentations for the user's fingers.

Mouse 12 may include other input devices 141 such as buttons 15 which are within easy reach of a user's fingers. Additional buttons, such as button 15a, may also be included on the top surface or on the side surfaces of mouse 12 for added functionality. Buttons 15 allow a user to input a command independently of the position of the mouse 12 in the provided degrees of freedom. For example, in a GUI, buttons are commonly used to select options once a cursor has been guided to a desired area or object on the screen using the position of the mouse. In one embodiment, the user can place his or her two middle fingers on buttons 15 and place the remaining fingers on the sides of mouse 12 (and at button 15a) to manipulate mouse 12 against forces generated by actuators 64. In addition, in some configurations with a smaller-size mouse 12, the fingers 247 of a user may move the mouse 12 and press buttons 15 while the palm 248 of the hand remains fixed or resting against a grounded surface. Since the fingers are more sensitive to output forces than the entire hand, forces of less magnitude may be output from the interface system 10 to the fingers and achieve an equivalent force sensation to higher magnitude forces applied to the entire hand (as with a joystick). Thus, less powerful actuators and less power consumption by the actuators is required when the user manipulates the mouse 12 with fingers alone.

Figure 7B:
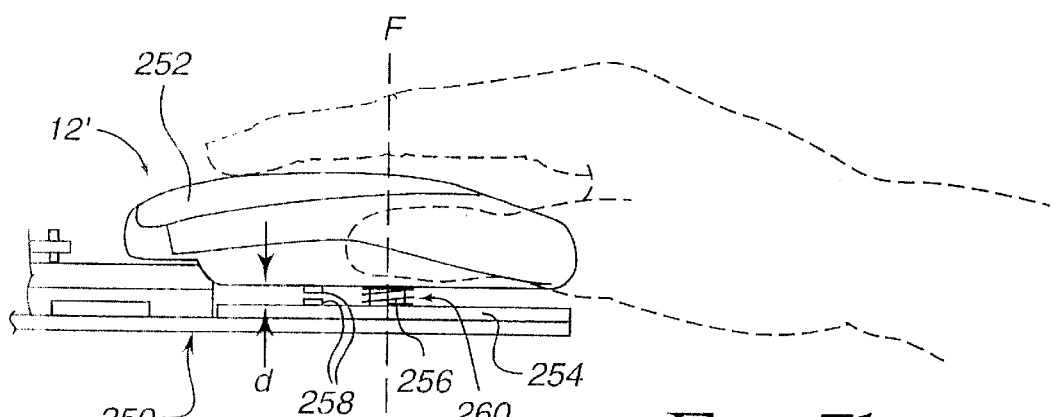
FIG. 7b is a side elevational view of the mouse of FIG. 7a showing a safety switch.

As shown in FIG. 7b, mouse 12 may also include a safety switch 150 (also known as a "deadman switch"). The safety switch preferably deactivates any generated forces on the puck when the puck is not in use and/or when the user desires to deactivate output forces. As described above, the safety switch can be implemented in a variety of ways. In FIG. 7b, a preferred way to implement a safety switch 150 is to use a hand-weight safety switch 250. As implemented, the user must activate or close the switch before actuators 64 are able to output forces. This is a safety feature that prevents the mouse 12 from unexpectedly moving and impacting the user when the user is not controlling the user object.

Mouse 12' including safety switch 250 includes a grip portion 252, a base 254, a spring 256, and switch contacts 258. Portion 252 may be shaped like mouse 12 described above, but can also be replaced with other types of user objects 12. Portion 252 can be moved up and down along axis F within a range distance d of the base 254 preferably on an extension member 260 or other similar guide. Distance d is preferably relatively small, such as 1 millimeter, and is exaggerated in FIG. 7b for clarity. Pre-loaded spring 186 preferably forces grip portion 252 away from base 254 in a direction indicated by arrow 262 to an "open" position when no weight is placed on portion 252. Preferably, a stop (not shown) coupled to the top of member 260 or to the bottom of portion 252 prevents the grip portion 252 from being detached from the base 254. A limit to movement of portion 252 in the direction of base 254 is provided by the physical engagement of the grip portion and base.

A z-axis force sensor can also be used to measure how hard the user is pushing down on the mouse 12. One example of such a sensor is shown in FIG. 4e. Other types of sensors also can be used, such as piezo electric sensors, force sensitive resistors, and strain gauges. Any z-axis pressure or force can also affect forces on the user object such as friction forces, as explained with reference to FIG. 4e. When using a force sensor as a safety switch, the microprocessor (or host) can check for a minimum threshold pressure on the user object; if the pressure is below the threshold, the actuators are deactivated.

Switch contacts 258 are provided between the base 254 and grip portion 252 of mouse 12'. Contacts 258 are connected by a bus to the host computer 18 or microprocessor 130, which can monitor when the contacts are touching. When the grip portion 252 is in the open position, contacts 258 are separated and no electrical current can flow between them, and thus no electrical current or power can flow to the actuators from the power supply. Alternatively, contacts 258 can be connected to microprocessor 130 or another selecting component which can detect the open state of the contacts and can deactivate actuators 64 with a safety disable signal when the open state is detected. The actuators 64 are thus prevented from outputting forces when the user does not have control of the grip portion 252 and the interface system 10.

When a user grasps portion 252, the weight of the user's hand forces the grip portion 252 down to engage the base 254. Switch contacts 258 connect from this engagement and allow current to flow between them. Contacts 258 complete the circuit from the actuators to the power supply, and power is thus allowed to flow from the power supply to the actuators. Alternatively, microprocessor 130 detects the closed contact condition and discontinues sending a safety disable signal to actuators 64. This allows the actuators 64 to be controlled and activated by host computer 18 and microprocessor 130 normally. When the user releases the grip portion from his or her grasp, the spring 256 forces the grip portion 252 away from base 254, which separates contacts 258 and deactivates the actuators.

The hand-weight safety switch has several advantages over other types of safety switches. The user can simply rest his or her fingers or hand on mouse 12' in a normal, comfortable fashion and still activate the safety switch due to the weight of the user's hand. Thus, the user need not cover or press an awkwardly-located switch in a particular location of the mouse.

In alternate embodiments, other types of safety switches may be used. For example, a mechanical button safety switch similar to buttons 15 can be provided which makes an electrical contact when the weight of the user's hand presses on the puck. Contact switches, light detectors, and other types of switches which the user contacts or covers during operation of the user object can be provided, but may be more awkward to use during operation of the user object since the user must constantly contact or cover a specific area of the user object or device housing. Hand-weight safety switch 252 can also be used to supplement a different type of safety switch.

Figure 7C:
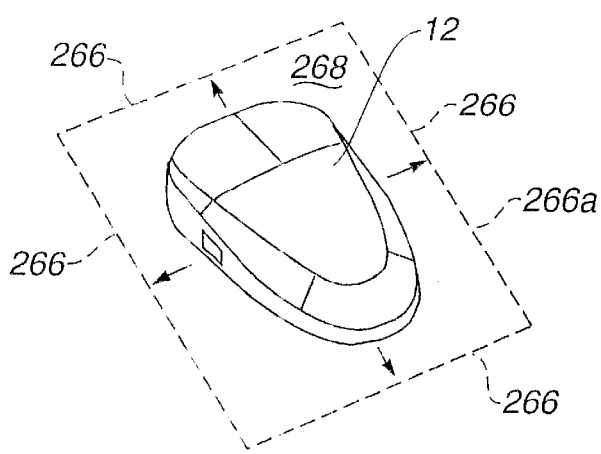

FIG. 7c is a diagram for illustrating an indexing feature of the present invention. The mouse 12 preferably has an "indexing mode" which allows the user to redefine the offset between the positions of the mouse 12 and a user-controlled graphical object, such as a cursor, displayed by host computer 18. Indexing is inherently provided with a traditional position control interface such as a mouse. For example, in a GUI, the position of the mouse controls the position of a cursor in the GUI. Sometimes, a limit to the mouse's movement is reached, such as a limit to available physical space, a limit to a mousepad, etc. In such a situation, the user typically lifts the mouse from the contacted surface and places the mouse in a different position to allow more room to move the mouse. While the mouse is off the contacted surface, no input is provided to control the cursor.

Mouse 12 of the present invention has a similar limit to movement in the provided planar workspace. The limit, in the described embodiment, is provided by guide opening 76 and guide pin 78, as detailed above. In other embodiments, the limits may be dictated by mechanical apparatus 102, actuators 64, or linkage 40; e.g., the limits of the movement of portions 80 of the voice coil actuators 64. The limits are indicated as dashed lines 266 in FIG. 7c such that the mouse 12 has a workspace 268 within the dashed rectangle (or circle or other shape, as desired). In the preferred embodiment, the workspace 268 is small (e.g., 0.9"x0.9"), since it has been found that very little workspace is needed to move a cursor across the full width or length of a display screen. Nevertheless, a limit 266 to the movement of mouse 12 may be reached in a situation where the user wishes to move the puck past the limit. For example, mouse 12 may reach the right limit 266a before the controlled cursor is fully moved to a desired location at the right of the screen. In other situations, the user might desire to reposition mouse 12 without providing any input to the graphical environment of host computer 18, such as to reposition mouse 12 to a more comfortable position, etc.

To allow movement past the limits 266, "indexing" is implemented. This allows the user to reposition the mouse 12 without moving the controlled graphical object or providing any other input to the host computer, thus allowing the user to redefine the offset between the object's position and the cursor's position. Since the mouse 12 does not contact or roll over a surface like a traditional mouse, the mouse 12 cannot simply be picked up and repositioned. In the present invention, indexing is achieved through an input device 141. Such input devices can include one or more buttons, switches, pressure sensors, optical sensors, contact sensors, voice recognition hardware, or other input devices. For example, a specialized indexing button can be provided which can be pressed by the user; such a button can be a traditional button 15 or 15a or a hand weight switch 250. As long as the indexing button is activated, the mouse 12 is in indexing mode and can be moved without providing any input to the host computer (e.g., without moving the controlled graphical object). When the button is released (or deactivated) and non-indexing mode is resumed, the position of the cursor is again controlled by the position of the mouse 12. Alternatively, the user might toggle indexing mode and non-indexing mode with one press of a button 15 or other input device. Thus, the user can move mouse 12 to a desired position in the planar workspace without providing input.

In one preferred embodiment, the functionality of the safety switch 250 and the indexing mode are integrated into one input device, since it is typically desirable to deactivate any output forces to the mouse 12 when indexing is being performed for safety reasons or ergonomic reasons, e.g. forces intuitively should not be output when indexing occurs. Preferably, the hand weight safety switch 250 shown in FIG. 7b can be used as both a safety switch and an indexing switch. For example, when the user places his or her fingers on mouse 12, the switch 250 is closed, allowing power to the actuators and forces to be output on the mouse. This also allows non-indexing mode to be active so that positions of cursor and mouse are directly mapped. If the user moves the mouse to a limit 266, the user then lifts up on the mouse or otherwise performs the indexing function. This opens switch 250, thereby disabling power to the actuators and engaging indexing mode. The user can move mouse 12 to another position using side motion (so as to not close switch 250), while the cursor remains fixed at its old position on the screen. When the mouse is at its new desired location, the user rests his or her fingers on the mouse 12 normally, thereby closing the switch 250. This allows indexing to be performed safely, without the need to provide a separate safety switch to deactivate the actuators 64.

If a z-axis force sensor is used for indexing, then the microprocessor or host can check for a threshold pressure. If the exerted pressure is below the threshold, indexing is active. A different threshold for indexing and for the safety switch can be implemented if desired; typically, the threshold for the safety switch would be lower. A local sensor might check for these threshold pressures, such as a Schmitt trigger, or the microprocessor can check for the threshold pressures. If the microprocessor checks, then the user preferably can input preferred thresholds to customize the interface device for his or her own use.

Indexing mode can be performed directly by the host computer 18. However, in the preferred embodiment, local microprocessor 130 performs the indexing function. For example, local processor 130 can determine when indexing mode is active, and simply not report the position of the mouse 12 to the host computer 18 while such mode is active. When non-indexing mode is active, processor 130 would resume reporting the position of the user object to the host. The host is thus completely ignorant of when indexing is performed, since it simply updates cursor position when it receives position data. The host does not have to detect or keep track of when indexing mode is active, thereby reducing its computational burden.

Figure 8A:
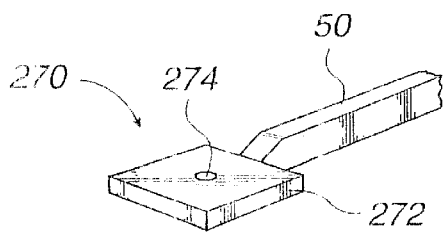
FIGS. 8a–8e are perspective views of alternate embodiments of the interface object for use with the interface system of FIG. 1.
Figure 8B:
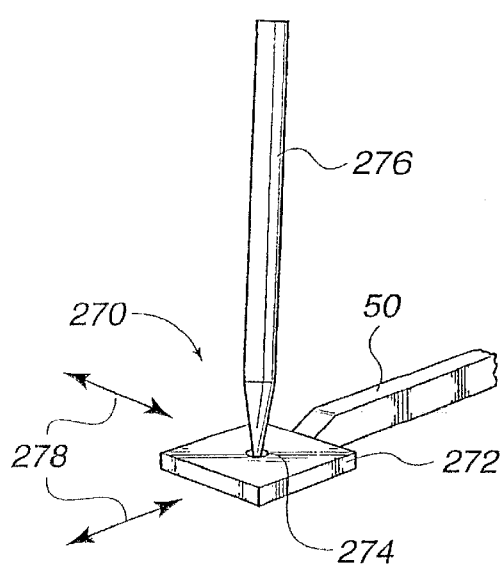

FIG. 8a is a perspective view of an alternate embodiment of user object 12. Object 12 is shown as a stylus-receiving user object 270, which can be coupled to any embodiment of mechanical apparatus 102, such as those embodiments presented above. Stylus-receiving user object 270 includes a stylus-receiving member 272, which is preferably a flat, small object that includes a stylus aperture 274. Member 272 may, for example, be coupled to object member 50 of the embodiment of mechanical apparatus 102. As shown in FIG. 8b, a stylus 276 or a similar article can be inserted into aperture 274 by a user. The user can then move the stylus 276 along a provided degree of freedom indicated by arrows 278, which causes member 272 to accordingly move in the same direction. Alternatively, stylus 276 can be permanently coupled to member 272.

The embodiment of FIGS. 7a–b can be used in a writing interface version of interface system 10 where the user uses the interface to write words input to a computer system, or in a pointing interface to direct and move computer-implemented objects such as a cursor. The member 272 alone can be considered the "user object" 12 in this embodiment. Alternatively, both stylus 276 and member 272 can collectively be considered user object 12, particularly in embodiments where stylus 276 is permanently fixed to member 272. In other embodiments, the member 272 can be detachable from mechanical apparatus 102 so as to allow different, interchangeable user objects 12 to be used as suited for particular applications.

Figure 8C:
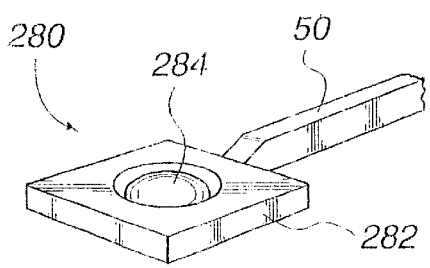
Figure 8D:
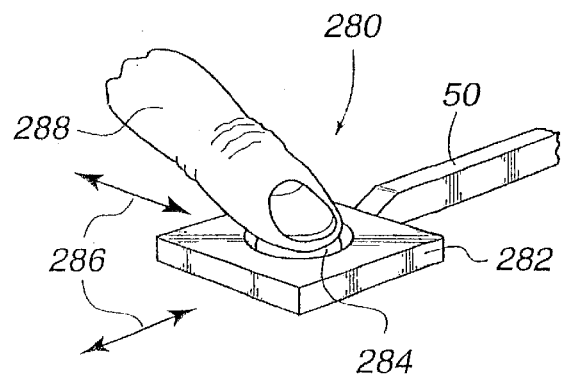

FIG. 8c is a perspective view of an alternate embodiment of user object 12 in which a finger-receiving user object 280 is provided. In this embodiment, a finger-receiving member 282, which includes a divot 284. Member 282 may be coupled to apparatus 102 similarly to the member 272 of FIG. 8a. As shown in FIG. 8d, a user may insert his or her finger 288 into divot 284 and thereby move member 222 in the provided degrees of freedom as indicated by arrows 286. Divot 284 allows the user's finger 288 to grip or cling to the member 282 when the user's finger is moved. In other embodiments, features other than or in addition to divot 284 can be provided on finger-receiving member 282 to allow the user's finger to cling to the object. For example, one or more bumps, apertures, or other projections can be provided. Also, other digits or appendages of the user can be received, such as a user's entire hand, foot, etc. The user object of FIGS. 7c–d can be used to allow the user to move, point to, or otherwise manipulate computer generated objects in an easy, natural fashion. The stylus- and finger-receiving objects of FIGS. 7a–7d can also be made interchangeable with the mouse object 12 so that the user can simply attach the desired user object for a particular application.

Figure 8E:
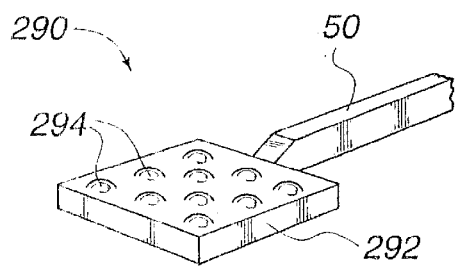

FIG. 8e is a perspective view of an alternate embodiment 290 of the finger-receiving object 280 of FIGS. 8c–8d. Object 290 includes a flat planar member 292 that, for example, may resemble a plastic card or other platform. Member 292 is (rigidly) coupled to object member 50, and may be rotatably coupled to the object member in some embodiments. The user may place one or more fingers on the planar member 292 similar to the object 280 and move it in a planar workspace. In addition, the planar member 292 can include a rubber or similar surface having friction to provide a grip or non-slippery contact between the user's fingers and the member. Also, the planar member 292 can be contoured or include bumps 294 or other protrusions to further promote the user's contact.

While this invention has been described in terms of several preferred embodiments, it is contemplated that alterations, permutations and equivalents thereof will become apparent to those skilled in the art upon a reading of the specification and study of the drawings. For example, other types of mechanical linkages can be provided between the mouse 12 and the electronic portion of the interface 14. In addition, other types of actuators, sensors, and user objects can be used in other embodiments. Furthermore, certain terminology has been used for the purposes of descriptive clarity, and not to limit the present invention. It is therefore intended that the following appended claims include all such alterations, permutations, and equivalents as fall within the true spirit and scope of the present invention.

What is claimed is:

1. A mouse interface device for interfacing a user's motion with a host computer and providing force feedback to said user, said mouse interface device comprising:

a mouse object contacted and manipulated by a user and moveable in a planar workspace with respect to a reference surface;

a planar linkage including a plurality of members rotatably coupled to each other, said linkage including a first base member rotatably coupled to said reference surface, a link member rotatably coupled to said first base member, a second base member rotatably coupled to said reference surface, and an object member rotatably coupled to said link member and rotatably coupled to said second base member, wherein said mouse object is coupled to one of said link member and said object member, and wherein said first base member and said second base member pivot about a single axis with respect to said reference surface;

two electromagnetic actuators providing forces in said planar workspace of said mouse object, said forces caused by interactions between an electric current and a magnetic field, wherein each of said actuators includes a coil portion and a magnet portion coupled to said ground surface through which said coil portion moves, wherein said base members each consist of one unitary piece, wherein a coil of one of said coil portions is integrated in each of said unitary pieces, and wherein said actuators are controlled from commands output by said host computer; and at least one sensor coupled to said reference surface and separate from said two actuators, said sensor detecting movement between said coil portion and said magnet portion of at least one of said actuators, wherein said sensor provides a sensor signal including information describing said movement from which a position of said mouse object in said planar workspace can be determined.

2. A mouse interface device as recited in claim 1 wherein said magnet portion of one of said actuators is coupled to said magnet portion of said other actuator such that a common flux path between said magnet portions is shared by both magnet portions.

3. A mouse interface device as recited in claim 1 wherein said first and second base members are coupled to a rotation point at a point between ends of said base members, where one end of each base member integrates a coil such that said coil is spaced from said rotation point of said member, thereby providing mechanical advantage to forces generated by said actuator on said base members.

4. A mouse interface device as recited in claim 1 wherein said at least one sensor includes an optical encoder, and wherein said ends of said first base member and said second base member include an encoder arc having a number of equally spaced marks provided, said marks being detected by said encoder when said member moves.

5. A mouse interface device as recited in claim 1 further comprising a stop mechanism for limiting movement of said mouse object in four directions in said planar workspace to a desired area.

6. A mouse interface device as recited in claim 5 wherein said stop mechanism includes a guide opening provided in said reference surface and a guide pin coupled to said linkage, wherein said guide pin engages sides of said guide opening to provide said limits to said movement in said planar workspace.

7. A mouse interface device as recited in claim 1 wherein said mouse object is supported by a support separate from said linkage and provided between said mouse object and said reference surface.

8. A mouse interface device as recited in claim 7 wherein said mouse object is supported by low friction Teflon pad.

9. An interface device for providing force feedback to a user of said interface device, wherein a host computer is coupled to said interface device and implements a graphical environment with which said user interacts, said interface device comprising:
- a user object physically contacted and manipulated by a user in two degrees of freedom with respect to a reference surface;
- a mechanical support linkage including a plurality of members, said support linkage being a closed loop five bar linkage coupled to said user object and providing said two degrees of freedom substantially in a single plane, said linkage including two base members coupled to said reference surface and rotatable about the same axis;
- a plurality of voice coil actuators, each of said actuators including a wire coil rigidly integrated with one of said base members of said linkage such that said wire coil rotates with said integrated base member, wherein said wire coil moves through a magnetic field provided by a plurality of grounded magnets, and wherein at least one housing provides a flux path and surrounds said magnets, wherein said magnets are stacked and share a magnetic flux path, each of said wire coils being coupled to an end of a different member of said support linkage, said coils guided through said magnetic field by said linkage; and
- at least one sensor detecting movement of said members having said wire coils, wherein said sensor includes an emitter that emits a beam of energy and a detector that detects said beam, wherein both said emitter and said detector of said sensor are coupled to said reference surface.

10. An interface device as recited in claim 9 wherein said at least one sensor includes two optical encoders, and wherein first ends of said base members are coupled to link members and second ends of said base members include an encoder arc having a number of equally spaced marks, said marks being detected by said encoders when said member moves.

11. An interface device as recited in claim 9 further comprising a support coupled to said user object that supports said user object on said reference surface in addition to said support linkage.

12. An interface device as recited in claim 9 wherein said two grounded actuators are coupled together and are provided as a single unit.

13. A force feedback mouse interface for interfacing with a host computer system implementing a graphical environment, the force feedback mouse interface comprising:
- a mouse object resting on a reference surface to be physically contacted by a user and moved in two degrees of freedom in a planar workspace, said workspace having predetermined limits to movement provided by a physical stop structure surrounding said planar workspace;
- a planar closed loop linkage coupling said mouse object to said reference surface and allowing movement of said mouse object in said two degrees of freedom, said linkage including a plurality of members, each of said members rotatably coupled to two others of said members or rotatably coupled to one of said members and to said surface;
- two grounded voice coil actuators, each of said actuators including a wire coil provided on a different member of said linkage, each of said wire coils pivoting about the same axis of rotation, wherein each of said actuators includes a plurality of grounded magnets in a flux path housing surrounding said wire coil, wherein said housing of one of said actuators is positioned above and contacting said housing of said other actuator, and wherein each of said actuators is receptive to a control signal operative to control an output force from said actuator on said member having said wire coil; and
- at least one grounded sensor, said sensor detecting motion of said mouse object in said two degrees of freedom, said sensor outputting a sensor signal indicative of said motion.

14. A force feedback mouse as recited in claim 13 further comprising a support resting on said reference surface that supports said mouse object.

15. A force feedback mouse interface as recited in claim 13 wherein said physical stop structure includes a guide opening provided in a housing and a guide pin coupled to said linkage, wherein said guide pin engages sides of said guide opening to provide said limits to said movement in said planar workspace.

16. A force feedback mouse interface as recited in claim 13 wherein said mouse object is also supported by a support separate from said linkage and provided between said mouse object and said reference surface.

17. A force feedback mouse interface as recited in claim 16 wherein said mouse object is supported by low friction pad.

18. An interface device for providing force feedback and interfacing with a host computer system implementing a graphical environment, the interface device comprising:
- a support base provided on a grounded surface, said base including a support surface provided above said grounded surface;

a mouse object resting on said support surface to be physically contacted by a user and moved in two degrees of freedom in a planar workspace, said workspace having predetermined limits to movement of said mouse object;

a planar closed loop linkage coupling said mouse object to said reference surface at one location on said reference surface and allowing movement of said mouse object in said two degrees of freedom, said linkage including a plurality of members rotatably coupled together by bearings, each of said members rotatably coupled to two others of said members or rotatably coupled to one of said members and to said surface, wherein a portion of said linkage is positioned beneath said support surface and wherein a portion of said linkage extends through said support surface and is coupled to said mouse object;

two grounded actuators, each of said actuators providing a force in said two degrees of freedom; and at least one grounded sensor, said sensors detecting motion of said mouse object in said two degrees of freedom, said sensor outputting a sensor signal indicative of said motion.

19. An interface device as recited in claim 18 wherein said bearings of said linkage include at least one bearing assembly providing a plurality of layers of balls in grooves.

20. An interface device as recited in claim 18 wherein said bearings of said linkage include at least one snap bearing that includes a cylindrical boss coupled to one member which rotates within a cylindrical cavity of another member, said boss held to said cavity by a spring force.

21. An interface device as recited in claim 18 wherein said bearings of said linkage include at least one snap bearing that includes a cylindrical cavity coupled to one member and a bearing assembly coupled to another member, said bearing assembly including a boss held to said cavity by a spring force, said bearing assembly including two bearings rotatable with respect to each other.

22. An interface device as recited in claim 18 wherein said bearings of said linkage include at least one bearing having a V-shaped edge on one member that rotates within a V-shaped groove of another member.

23. An interface device as recited in claim 18 wherein said portion of said linkage extending through said support surface extends through a guide opening in said support surface.

24. An interface device as recited in claim 18 wherein said guide opening functions as a stop mechanism wherein said portion of said linkage extending through said opening engages sides of said guide opening to provide said predetermined limits to said movement of said mouse object.

25. An interface device as recited in claim 18 wherein said linkage includes a base member coupled to said ground surface and a link member coupled to said mouse object, wherein a portion of said link member extends through said support surface and is coupled to said mouse object.

* * * * *